US010932477B2

(12) United States Patent
Coquet et al.

(10) Patent No.: US 10,932,477 B2
(45) Date of Patent: Mar. 2, 2021

(54) PEPTIDE AND SACCHARIDE HYDROLYSATE OF COCOA BEANS, COSMETIC COMPOSITIONS CONTAINING SAME, AND COSMETIC USES OF SAME

(71) Applicants: ISP INVESTMENTS LLC., Wilmington, DE (US); JAFER ENTERPRISES R&D, S.L., Barcelona (ES)

(72) Inventors: Corinne Coquet, Cipieres (FR); Catherine Gondran, Seillans (FR); Isabelle Imbert, Cannes (FR); Joel Mantelin, Cannes (FR); Nouha Domloge, Opio (FR); Sébastien Garnier, Le Rouret (FR); Jérémie Borsotto, Pegomas (FR); Esmeralda Cicchetti, Castets (FR); Florian Labarrade, Antibes (FR)

(73) Assignees: ISP INVESTMENTS LLC, Wilmington, DE (US); JAFER ENTERPRISES R&D, S.L., Barcelona (ES)

( * ) Notice: Subject to any disclaimer, the term of this patent is extended or adjusted under 35 U.S.C. 154(b) by 311 days.

(21) Appl. No.: 16/084,783

(22) PCT Filed: Mar. 15, 2017

(86) PCT No.: PCT/EP2017/056084
§ 371 (c)(1),
(2) Date: Sep. 13, 2018

(87) PCT Pub. No.: WO2017/157998
PCT Pub. Date: Sep. 21, 2017

(65) Prior Publication Data
US 2019/0075813 A1 Mar. 14, 2019

(30) Foreign Application Priority Data
Mar. 16, 2016 (FR) ...................... 1600441

(51) Int. Cl.
| A23G 1/30 | (2006.01) |
| A61K 8/64 | (2006.01) |
| A61Q 19/08 | (2006.01) |
| A61K 8/97 | (2017.01) |
| A23L 33/105 | (2016.01) |
| A23L 33/18 | (2016.01) |
| A61K 8/60 | (2006.01) |
| C12N 9/42 | (2006.01) |
| C12N 9/24 | (2006.01) |

(52) U.S. Cl.
CPC .............. *A23G 1/30* (2013.01); *A23L 33/105* (2016.08); *A23L 33/18* (2016.08); *A61K 8/60* (2013.01); *A61K 8/645* (2013.01); *A61K 8/97* (2013.01); *A61Q 19/08* (2013.01); *C12N 9/248* (2013.01); *C12N 9/2437* (2013.01); *A23V 2002/00* (2013.01); *A61K 2800/522* (2013.01); *A61K 2800/805* (2013.01); *C12Y 302/01003* (2013.01); *C12Y 302/01004* (2013.01); *C12Y 302/01008* (2013.01); *C12Y 302/01015* (2013.01)

(58) Field of Classification Search
CPC .......... A23V 2002/00; A23V 2200/318; A23V 2250/21; A23V 2250/55; A23G 1/30; A23L 33/105; A23L 33/18; A61K 2800/522; A61K 2800/805; A61K 8/60; A61K 8/645; A61K 8/97; A61Q 19/08; C12N 9/2437; C12N 9/248; C12Y 302/01003; C12Y 302/01004; C12Y 302/01008; C12Y 302/01015
See application file for complete search history.

(56) References Cited

FOREIGN PATENT DOCUMENTS

| CN | 102687838 A | * | 9/2012 |
| CN | 102687838 A | | 9/2012 |
| EP | 2322041 A1 | | 5/2011 |
| EP | 2517567 A1 | | 10/2012 |
| WO | 2008/015341 A2 | | 2/2008 |
| WO | 2008/059064 A1 | | 5/2008 |

OTHER PUBLICATIONS

International Search Report issued in PCT/EP2017/056084 dated Apr. 19, 2017 (9 pages).
Written Opinion issued in PCT/EP2017/056084 dated Apr. 19, 2017 (9 pages).
Martorell et al., "A cocoa peptide protects Caenorhabditis elegans from oxidative stress and β-amyloid peptide toxicity", PLoS One. May 13, 2013;8(5):e63283. doi: 10.1371/journal.pone.0063283. Print 2013.
Sarmadi et al., "Antioxidant and angiotensin converting enzyme (ACE) inhibitory activities of cocoa (Theobroma cacao L.) autolysates", Food Research International, vol. 44, Issue 1, Jan. 2011, pp. 290-296, Abstract.
Fuziwara, et al., "Visible radiation affects epidermal permeability barrier recovery: selective effects of red and blue light." J Invest Dermatol. May 2008; 128(5):1335-6.

(Continued)

*Primary Examiner* — Aaron J Kosar
(74) *Attorney, Agent, or Firm* — FisherBroyles, LLP; Susan M. Oiler

(57) ABSTRACT

The invention relates to a peptide and saccharide hydrolysate of *Theobroma cacao* L. (cocoa) beans, to a method for preparing same, to cosmetic compositions containing same, and to cosmetic uses thereof particularly for protecting skin from blue light and/or for combatting the appearance of signs of aging and photoaging of the skin.

18 Claims, 5 Drawing Sheets

(56) References Cited

OTHER PUBLICATIONS

Godley et al., "Blue light induces mitochondrial DNA damage and free radical production in epithelial cells." J Biol Chem. Jun. 3, 2005; 280(22):21061-6.

Seko et al., "Blue light-induced apoptosis in cultured retinal pigment epithelium cells of the rat." Graefes Arch Clin Exp Ophthalmol. Jan. 2001; 239(1):47-52.

Katz, ML, "Potential role of retinal pigment epithelial lipofuscin accumulation in age-related macular degeneration." Arch Gerontol Geriatr. May-Jun. 2002; 34(3):359-70.

Kuse et al., "Damage of photoreceptor-derived cells in culture induced by light emitting diode-derived blue light", Sci Rep. Jun. 9, 2014; 4:5223.

Fisher et al., "Blue light irradiation suppresses dendritic cells activation in vitro." Exp Dermatol. Aug. 2013; 22(8):558-60.

Gold et al., "Clinical Efficacy of Self-applied Blue Light Therapy for Mild-to-Moderate Facial Acne." J Clin Aesthet Dermatol. Mar. 2009; 2(3):44-50.

Haltaufderhyde et al., "Opsin expression in human epidermal skin. Photochem Photobiol." Jan.-Feb. 2015; 91(1):117-23.

Poletini et al., "Nonvisual Opsins and the Regulation of Peripheral Clocks by Light and Hormones." Photochem Photobiol. Sep.-Oct. 2015; 91(5):1046-55.

Li et al., "CLOCK is required for maintaining the circadian rhythms of Opsin mRNA expression in photoreceptor cells." J Biol Chem. Nov. 14, 2008; 283(46):31673-8.

Langton et al., "A new wrinkle on old skin: the role of elastic fibres in skin ageing." Int J Cosmet Sci. Oct. 2010; 32(5):330-9.

Elfenbein et al., "Syndecan-4 signaling at a glance." J Cell Sci. Sep. 1, 2013; 126(Pt 17):3799-804.

\* cited by examiner

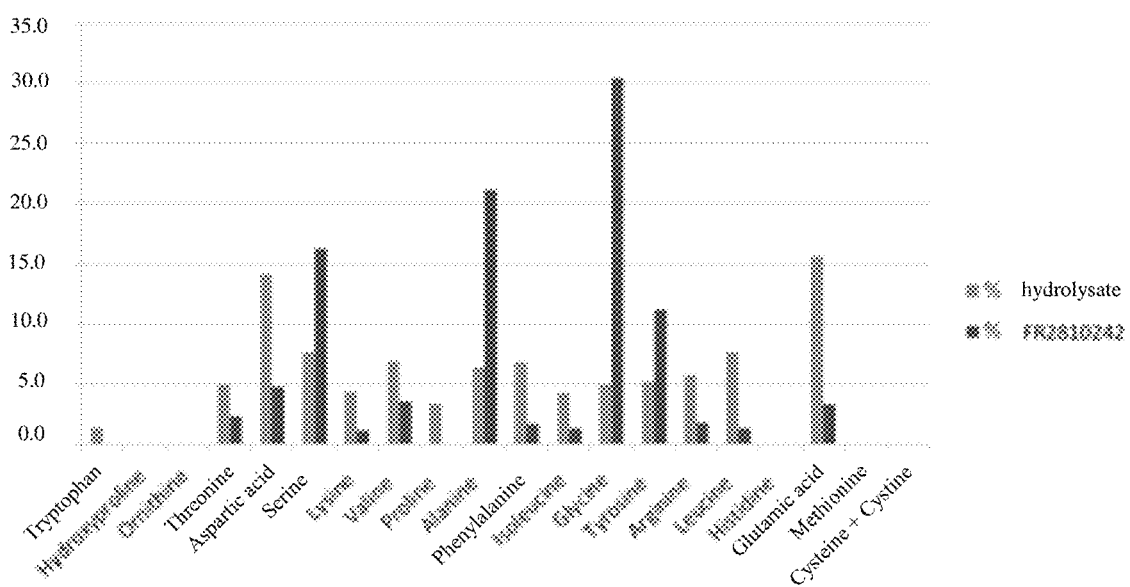

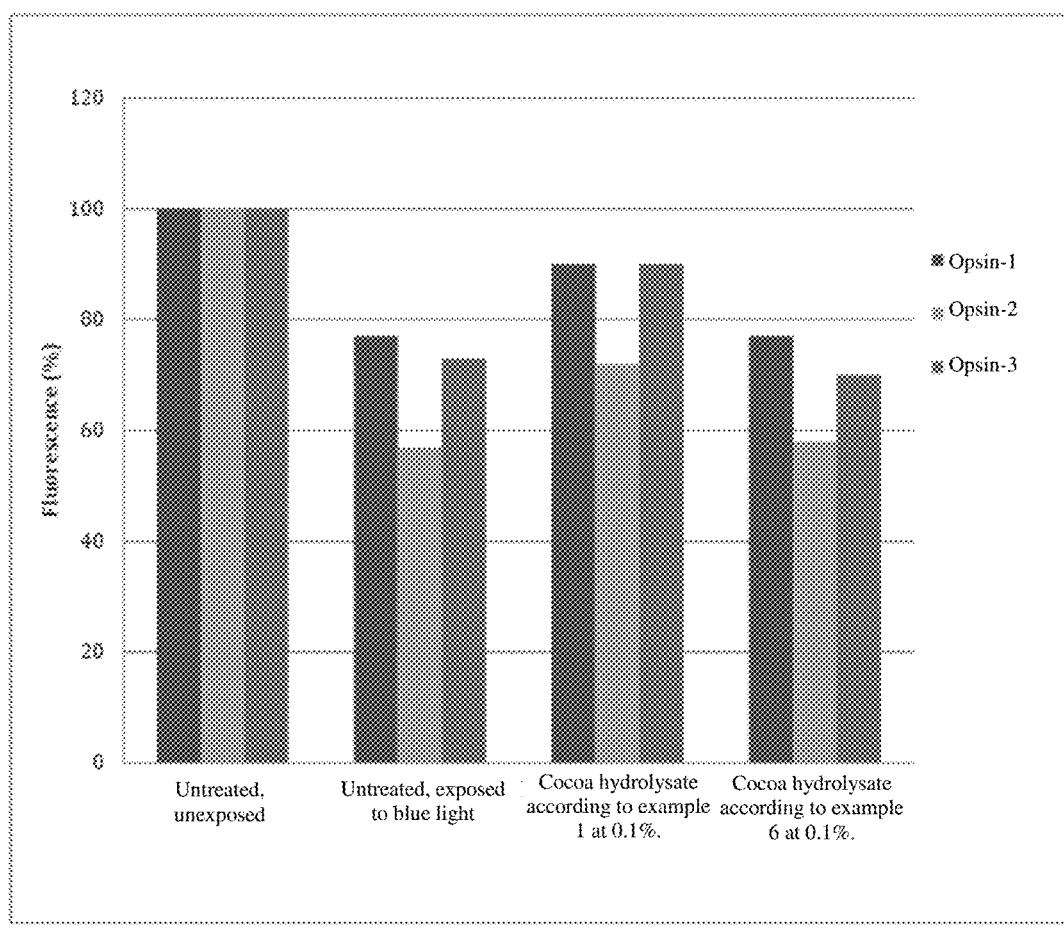

PEPTIDE AND SACCHARIDE HYDROLYSATE OF COCOA BEANS, COSMETIC COMPOSITIONS CONTAINING SAME, AND COSMETIC USES OF SAME

CROSS-REFERENCE TO RELATED APPLICATIONS

The present invention is filed under 35 U.S.C. § 371 as the U.S. national phase of International Patent Application No. PCT/EP2017/056084, filed Mar. 15, 2017, which designated the United States, and which claims the benefit of French Patent Application No. 1600441, filed Mar. 16, 2016, which is hereby incorporated in their entirety including all tables, figures, and claims.

The invention relates to a peptide and saccharide hydrolysate of *Theobroma cacao* L. (cocoa) beans, to a method for preparing same, to cosmetic compositions containing same, and to cosmetic uses thereof particularly for protecting skin from blue light.

Blue light represents a portion of visible light between 400 and 495 nm. It is the most high-energy portion of the visible spectrum. Most of the blue light received originates from the sun. In our interior environment, we are increasingly exposed to artificial blue light from LEDs (Light-Emitting Diodes) present in lighting, and in smartphone, tablet, computer and television screens.

The photons of visible light are captured by the photoreceptors on the cells of the retina, initiating the phototransduction mechanism. These photoreceptors, referred to as opsins, are coupled to the G proteins and contain a chromophore, 11-cis retinal, which undergoes a photoisomerization reaction into all-trans retinal, resulting in a signal transduction cascade.

The perception of light acts on the organism by two routes: the primary optical route which includes the visual effects, and the retinohypothalamic route which is followed by biological effects such as the secretion of melatonin, the regulation of body temperature, the expression of circadian genes.

Studies have been conducted on the damage generated by blue light on the cells of the retina. Exposure to visible light produces reactive oxygenated species in the epithelial cells of the retina, inducing mitochondrial DNA damage and possibly resulting in apoptosis of these cells2, 3. These alterations have been shown to be associated with the development of age-related macular degeneration, during which an accumulation of lipofuscin in the cells of the retina occurs4.

In addition, it has been demonstrated recently that blue light induces the accumulation of opsins in murine retinal cells, leading to cell damage5.

Another effect of blue light from the use of devices such as touch tablets has been reported. The use of devices of this type before falling asleep modifies the melatonin level and leads to a shift in the circadian rhythm 6. To counter the harmful effects of blue light, several optical brands producing devices containing LEDs have developed glasses or screens that block the wavelengths corresponding to blue.

Blue light also has effects on the skin. It has been demonstrated on keratinocytes and endothelial cells of human skin that blue light exerts an anti-proliferative effect and promotes the differentiation of the keratinocytes7. In addition, it suppresses the maturation of the dendritic cells8. These properties have led to the use of blue light in the treatment of hyper-proliferative and/or inflammatory skin diseases such as psoriasis, atopical dermatitis or eczema.

In addition, the exposure to blue light of skin fragments with previously altered barrier function has shown a delay in the recovery of the skin barrier, in particular concerning the lipids secreted at the interface between the stratum corneum and the stratum granulosum. This result has not been observed with other wavelengths of the visible spectrum, which suggests a specific activity of blue light in connection with the homeostasis of the skin barrier1.

Concerning the treatment of acne, exposure to blue light creates photoexcitation of the bacterial porphyrin of *Propionibacterium acnes*, leading to the elimination of the bacterium9.

Very recently, the expression of the opsin receptors OPN1-SW, OPN2, OPN3 and OPN5 has been identified in keratinocytes and melanocytes, suggesting that they play a role in phototransduction in skin cells10. The signals resulting from the activation of opsins in skin cells generate nonvisual effects including the regulation of the circadian genes11.

Considering the harmful effects that blue light can produce on the skin, it seems important to be able to develop a cosmetic composition which can be used for protecting the human skin from blue light.

Surprisingly, the Applicants have developed a novel method of extraction from cocoa beans, enabling the development of a peptide- and saccharide-rich extract which has proven to exhibit a protective activity with regard to blue light by improving the barrier function of the skin as well as a preventive activity against the appearance of aging of the skin.

The cocoa tree, also referred to as "Cocoa," is a small evergreen tree of the genus *Theobroma* of the Sterculiaceae family according to the classical classification or the Malvaceae family according to the phylogenetic classification. The cocoa tree is a tropical species originating from Mexico which was domesticated approximately 3000 years ago. It is a cauliflorous evergreen tree having a height of 10 to 15 meters, generally trimmed to 6 or 8 meters. It flowers starting at 3 years and produces flowers, fruits and leaves throughout the year. Annually, the tree can produce up to 100,000 flowers of white or slightly pink color. The flowers appear throughout the year on swellings on the wood of the tree, referred to as floral cushions. Consequently, flowers and fruits are found at the same time on the tree. The fruits of the trees, referred to as "pods," are large elongate berries. Each pod can weigh up to 400 g for a length of 15 to 20 cm. They have the particular feature of growing both on the main branches but also directly on the tree trunk. Their features are highly variable from one population to another, but also within the same population. The maturation of the fruits takes 5 to 7 months, depending on the genotypes. On average, one tree yields approximately 150 pods per year. The pods contain numerous seeds (between 25 and 75) which are grouped in spikes and called cocoa beans, and which are rich in starch, fats and alkaloids.

The cocoa beans are grouped in the center of the pod forming a mass comprising five rows corresponding to the five locules of the ovule. They have a variable ovoid-flattened shape and a length of about 25 mm, a width of about 15 mm and a thickness of about 8 mm. When fresh, they are sticky, since they are surrounded by a white pulp referred to as mucilage. The kernel of the cocoa bean is formed by a large embryo which comprises two cotyledons folded over themselves. It has a variable color ranging from white to dark violet depending on the varieties. It is wrapped by a seed coat of pink or pale red color. It is known that the cocoa beans contain approximately 50% fat referred to as cocoa butter, 5% water, 7% starch, 4% cellulose, 2% theobromine, 20% proteins, and 6% mineral substances.

It is known that cocoa has stimulating, tonic, nutritional and anti-stress effects, and various substances have been extracted from cocoa because of such properties. In cosmetics in particular, the cocoa butter from *Theobroma cacao* is used for its nourishing effect on the skin. The butter contains 53% fat (triglycerides comprising mainly oleic, stearic and palmitic acids) having super-nutritious qualities, its specific feature is that it is rich in unsaponifiables consisting of phytosterols and squalene. The first have an antioxidizing, cicatrizing and soothing action (against burns and chapping). The second, which is naturally present in the skin and in sebum, helps regenerate the lipid cement of the stratum corneum. This is the reason why cocoa butter is found as ingredient in massage butters for the skin as well as in hydrating, soothing and protecting balms. It is also valued in the care of very dry and unruly hair, as well as in the care of split ends.

Moreover, from the patent document FR2810242, a cosmetic and/or dermatological composition based on a cocoa protein extract comprising at least polyphenols, amino acids and an unsaponifiable fraction is known. Said compositions are useful for the treatment and the prevention of the signs of aging of the skin. In this document, the entire cocoa bean is used, in particular the cocoa butter, in order to obtain, after total enzymatic hydrolysis of the proteins, a mixture including 0.5-3% or 0.5-5% unsaponifiables, amino acids and polyphenols.

Moreover, from the patent document WO20080153341, a cosmetic composition is known, comprising a cocoa bean extract for promoting the pigmentation of body hair and/or cranial hair. The method for preparing the bean extract comprises the elimination of the lipids, the nucleic acids and the sugars of the bean. The method for obtaining the bean extract is centered on an enzymatic hydrolysis of the proteins in order to generate polypeptides, peptides and free amino acids.

In addition, from the patent document US2013/0035291, a bioactive product is known, comprising peptides with 5 to 20 amino acids originating from a cocoa hydrolysate, said product being intended for consumption and for treating neurodegenerative diseases. The method used in this document makes it possible to obtain specific purified, sugar-free peptide fractions.

The extraction method according to the present invention, developed by the Applicants using cocoa beans, is novel in comparison to the above-cited documents. This method is optimized for selecting and guaranteeing a high content of target molecules of interest including particular peptides and saccharides in the hydrolysate obtained from the cocoa beans. The peptide and saccharide hydrolysate according to the invention does not comprise unsaponifiable molecules or free amino acids, and the traces of polyphenols present in the hydrolysate confirm a different profile from that of the patent WO200195872.

Thus, a first subject matter of the invention is a peptide and saccharide hydrolysate of *Theobroma cacao* L. beans comprising predominantly peptides and saccharides.

In addition, a second subject matter of the invention is a method for preparing a peptide and saccharide hydrolysate of *Theobroma cacao* L. beans according to the invention, including the following steps according to which:
 a) crushed *Theobroma cacao* L. beans are dispersed in an aqueous phase;
 b) an enzymatic treatment of the aqueous dispersion obtained in step a) is carried out;
 c) the recovery of the enzymatic hydrolysate by solid/liquid separation is carried out,
 d) the hydrolysate is purified by ultrafiltration and nanofiltration, then optionally;
 e) a lyophilization of the hydrolysate obtained in step d) is carried out.

A third subject matter of the invention is a cosmetic composition, characterized in that it comprises, as active protective agent, an effective quantity of a hydrolysate of *Theobroma cacao* L. beans according to the invention, and a physiologically acceptable medium.

Finally, a fourth subject matter of the invention is a cosmetic use of a composition according to the invention, for protecting the skin from the harmful effects of blue light, in particular from oxidative stress generated by blue light, in order to improve the barrier function of the skin and to combat the appearance of signs of aging of the skin and photoaging of the skin.

The invention and the advantages proceeding therefrom will be understood better upon reading the description and the non-limiting embodiments which follow, drafted in view of the appended figures in which:

FIG. 1B represents the comparison: of the aminogram of
 the hydrolysate according to the invention, carried out
 by total hydrolysis of the peptides with a strong acid
 such as hydrochloric acid 6 N for 24 to 48 hours, with
 the aminogram given in the document FR2810242.

FIG. 2 represents the level of opsin-1, opsin-2 and opsin-3 after exposure to blue light (425 nm and 470 nm)

Figure 3A:
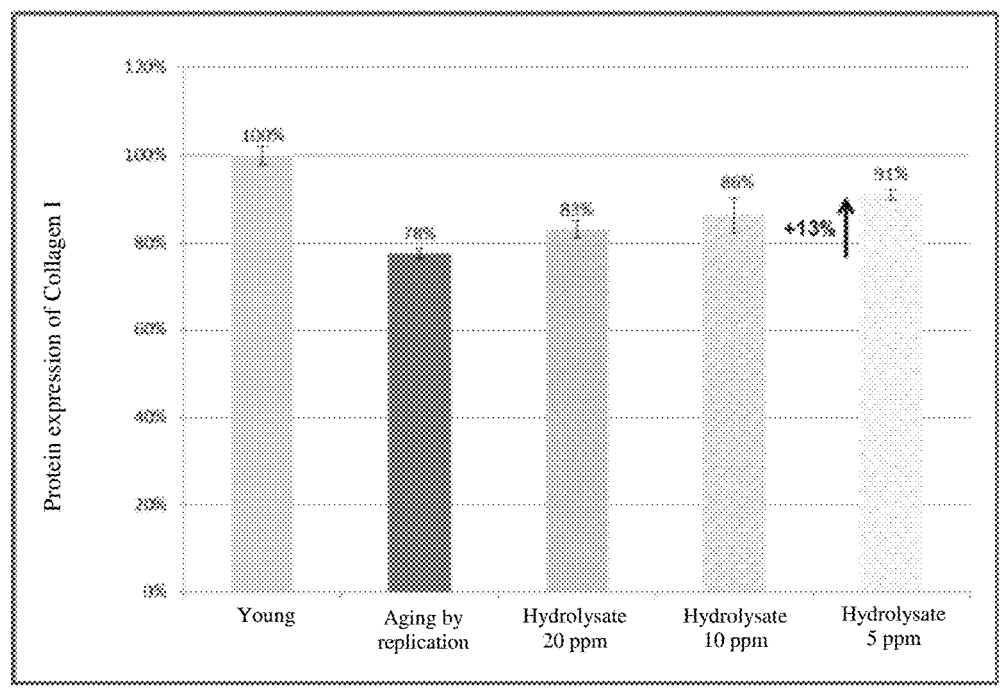
Figure 3B:
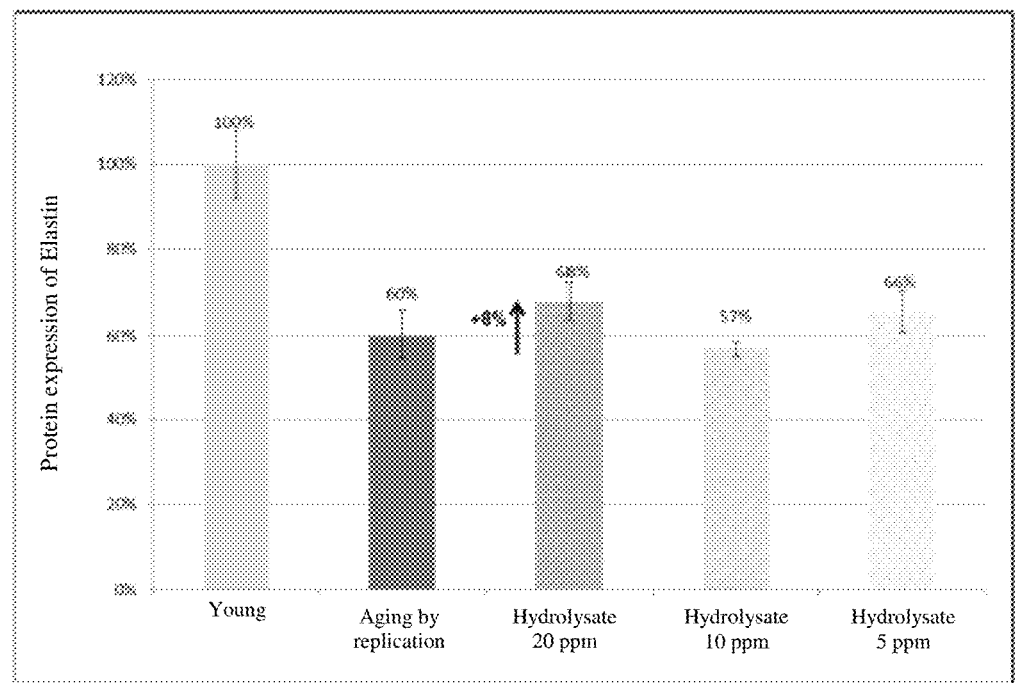
Figure 3C:
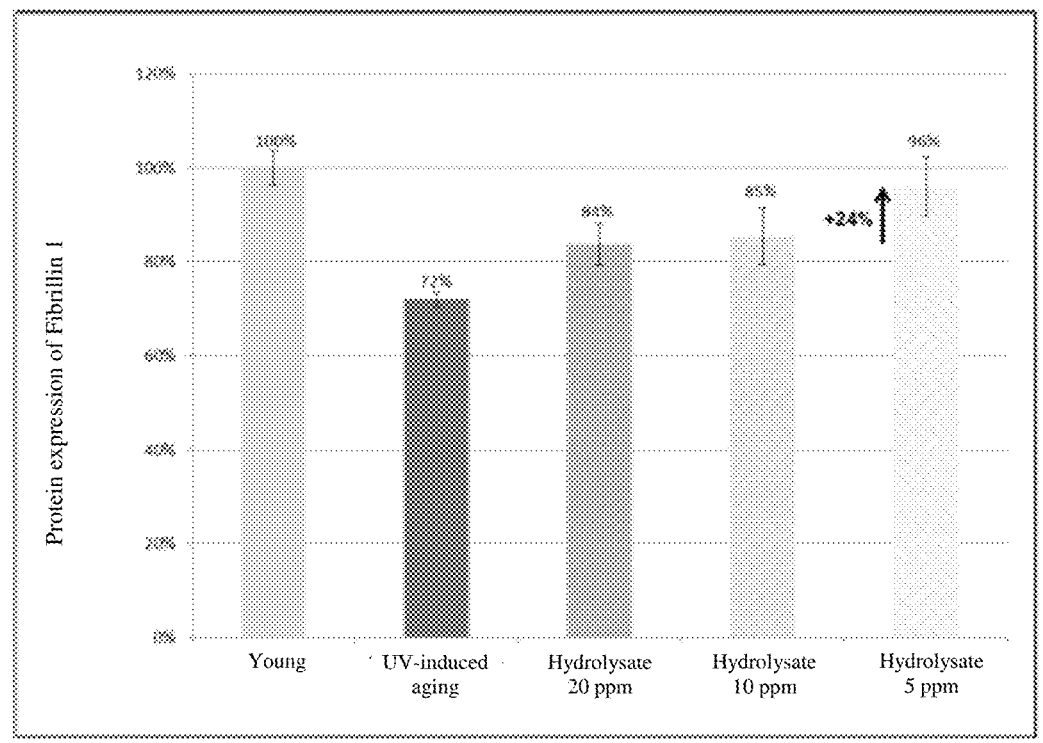
Figure 3D:
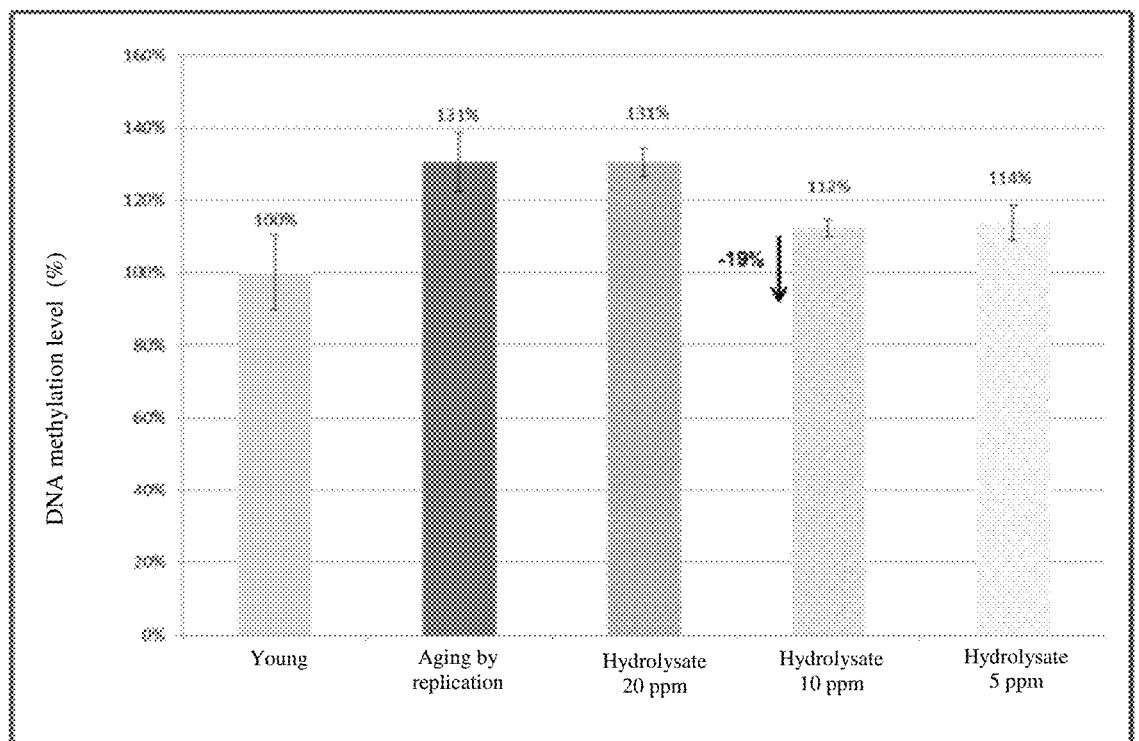

FIG. 3A represents the quantification of the expression of collagen 1 by the cocoa hydrolysate according to the invention FIG. 3B represents the quantification of the expression of elastin by the cocoa hydrolysate according to the invention FIG. 3C represents the quantification of the expression of fibrillin-1 by the cocoa hydrolysate according to the invention FIG. 3D represents the results of the cocoa hydrolysate according to the invention on the methylation of DNA.

In this description, unless otherwise specified in the text, it is understood that:
 when an interval is given, it includes the upper and lower
  limits of said interval,
 the % are expressed in weight/weight in the text, unless
  indicated otherwise.

Moreover, in the description, the expressions "peptide and saccharide hydrolysate of *Theobroma cacao* L. bean" or "peptide and saccharide hydrolysate" or "cocoa hydrolysate according to the invention" or "hydrolysate" are used interchangeably.

In the present invention,

"effective quantity" is understood to mean the quantity of active molecules necessary for obtaining the desired result, namely for making it possible in particular to obtain protection of the skin from blue light, without said quantity being toxic.

"predominantly of peptides and saccharides" is understood to mean a quantity of peptides and saccharides greater than 50%, preferably greater than 60%, even more preferably greater than 70% and possibly reaching about 90% (weight/weight), preferably 90% of the weight of the dry matter.

"peptide and saccharide hydrolysate" is understood to mean a hydrolysate comprising predominantly or essentially peptides and saccharides (mono- and oligosaccharides). The proteins and polysaccharides naturally present in the beans have been hydrolyzed to peptides, oligosaccharides and monosaccharides, the hydrolysis is advantageously an enzymatic hydrolysis.

"topical application" denotes the fact that the active substance according to the invention or a composition containing it is applied or spread on the surface of the skin, of a mucosal membrane or of keratinized skin appendages.

"cosmetically acceptable" is understood to mean that the active substance according to the invention or a composition containing it is suitable for coming in contact with the skin or a mucosal membrane without causing toxicity or intolerance reactions.

"physiologically acceptable" is understood to mean suitable for topical use in contact with the human skin, or for a use by other routes of administration, for example, the oral route or injection into the skin, without any risk of toxicity, incompatibility, instability, allergic response.

Thus, a first subject matter of the invention is a peptide and saccharide hydrolysate of Theobroma cacao L. beans comprising predominantly peptides and saccharides.

The hydrolysate according to the invention is obtained from Theobroma cacao L. beans, as starting material, which can include either the bean alone or the bean and its shell; it is preferable to use beans including the bean and its shell.

The beans used are dried beforehand and may be fermented or non-fermented. In a preferred embodiment according to the invention, the beans used are non-fermented and dried Theobroma cacao L. beans.

The harvested, washed and dried Theobroma cacao L. beans preferably come from Peru. They can originate from a mixture of various varieties or from at least one of the three varieties Criollo, Forastero and Trinitario.

In a preferred embodiment according to the invention, the beans originate from the Criollo variety and more particularly the Porcelana sub-variety. Moreover, the cocoa beans are not subjected to the essential steps of the chocolate production process, that is to say fermentation and roasting, since these steps have a harmful effect on the proteins and the sugars for this application.

In a preferred embodiment according to the invention, the peptide and saccharide hydrolysate according to the invention is obtained by an enzymatic treatment carried out with at least one carbohydrase and at least one protease. The enzymatic treatment is carried out in two steps, a first treatment uses the carbohydrases and leads primarily to disaccharides and monosaccharides, then a second treatment uses proteinases to obtain the peptides.

In an even more preferred embodiment of the invention, the carbohydrase is selected from the pectinases, the cellulases, the arabanases, the hemicellulases, the xylanases and the β-glucanases and the protease is of alkaline, neutral or acidic type, preferably of alkaline type with endopeptidase activity.

Advantageously, the carbohydrase will be a cocktail of carbohydrases, including at least a polygalacturonase, a pectin methyl esterase, a beta glucanase, a beta mannanase, a beta glucosidase, a cellulase, a hemicellulase, an arabanase and a xylanase.

The nonlyophilized cocoa hydrolysate according to the invention comprises from 20 to 70% peptides and from 5 to 40% saccharides. The lyophilized cocoa hydrolysate without drying support according to the invention comprises more than 90 percent of dry matter comprising from 20 to 70% peptides and from 5 to 40% saccharides.

According to another very preferred embodiment of the invention, the peptides and saccharides present in the hydrolysate according to the invention have a molecular weight from 200 Da to 10 kDa.

Advantageously, the hydrolysate according to the invention contains no unsaponifiables.

Also advantageously, the hydrolysate according to the invention does not include free amino acids.

Figure 1A:
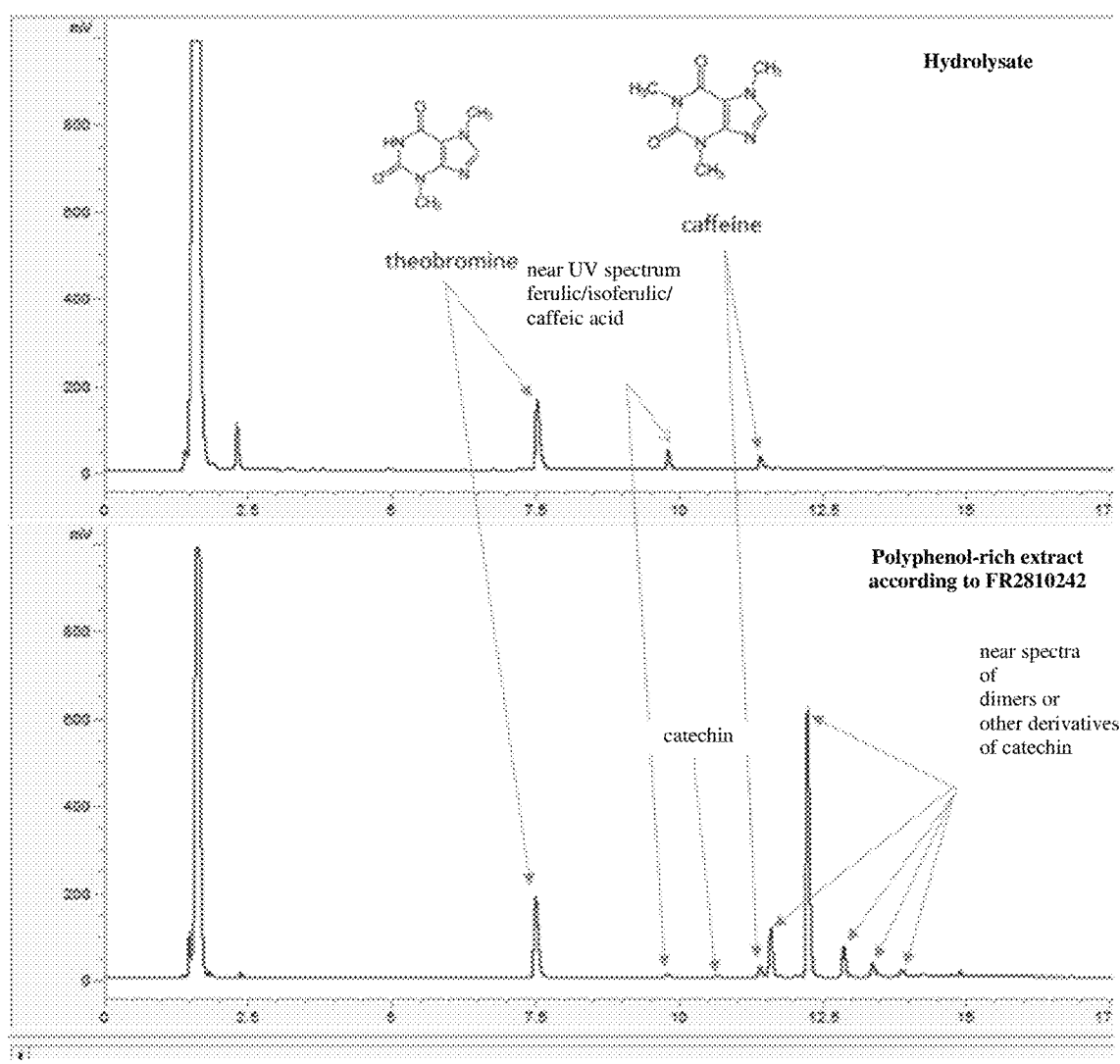
FIG. 1A represents the comparison: of the polyphenolic profiles of the hydrolysate according to the invention and of the polyphenol-rich water-alcohol extract according to FR2810242.

Finally, the hydrolysate according to the invention comprises a maximum of 0.05% polyphenols, which are predominantly molecules of the methylxanthines type, as indicated in FIG. 1A.

A second subject matter of the invention is a method for preparing a peptide and saccharide hydrolysate of the Theobroma cacao L. beans according to the invention, including the following steps according to which:

a) crushed Theobroma cacao L. beans are dispersed in an aqueous phase;

b) an enzymatic treatment of the aqueous dispersion obtained in step a) is carried out;

c) the enzymes are denatured by thermal treatment d) the recovery of the enzymatic hydrolysate is carried out by a solid/liquid separation, e) the hydrolysate is purified by ultrafiltration and nanofiltration, then optionally;

f) a lyophilization of the hydrolysate obtained in step e) is carried out.

The crushed Theobroma cacao L. beans used in step a) of the method according to the invention are first harvested, washed, dried and then delipidated by pressing to produce a cocoa bean cake. This cake is used for carrying out step a) of the method according to the invention.

Drying is understood to mean the phase after harvesting during which the beans are dehydrated in order to sufficiently reduce the water content of the beans to guarantee conditions that are favorable for storage or subsequent transformation of the beans.

For example, the beans can be dried naturally by exposure to the open air (in the sun or in the shade) for a duration of at most 10 to 20 days, or advantageously they can be gently dried artificially in a dryer with blown hot air, with regulation of the relative humidity, at a temperature between 40° C. and 60° C.

Preferably, after having been advantageously washed, the beans are dried, then crushed or cryocrushed and delipidated.

Delipidated beans refers to all the methods for eliminating all or part of the lipids of the cocoa beans, such as solid/liquid extraction with a volatile solvent, extraction with a supercritical fluid, or pressing.

In step a) of the method according to the invention, the beans and in particular the press cake is preferably dissolved in water at 10% dry matter.

The enzymatic treatment according to step b) of the method according to the invention is advantageously carried out in two steps, a first treatment uses the carbohydrases to hydrolyze the walls of the plant cells, then a second treatment uses proteinases to hydrolyze the proteins.

In a preferred embodiment of the method according to the invention, the carbohydrase is selected from the pectinases, cellulases, arabanases, hemicellulases, xylanases and β-glucanases, and the protease, of alkaline, neutral or acidic type, is preferably of alkaline type with an endopeptidase activity.

Advantageously, the carbohydrase will be a cocktail of carbohydrases, including at least a polygalacturonase, a pectin methyl esterase, a beta glucanase, a beta mannanase, a beta glucosidase, a cellulase, a hemicellulase, an arabanase and a xylanase.

The enzymes used in step b) of the method according to the invention advantageously constitute from 0.1% to 3.0% by weight with respect to the weight of the beans to be treated.

In a preferred embodiment according to the invention, more pectinases than cellulases will be used. It is thus preferable to use a 2:1 ratio of pectinases with respect to the cellulases.

The step c) of denaturation of the enzymes is carried out at a temperature between 80 and 90° C. for a duration of 15 minutes to 2 hours, the thermal treatment conditions preferably are 85° C. for 45 minutes.

Preferably, during the different steps a) to d) of the method according to the invention, the temperature is between 20 and 90° C. and the pH is between 3.0 and 11.0.

The recovery of the enzymatic hydrolysate carried out according to step c) of the method according to the invention is carried out by performing a solid/liquid separation by different methods known to the person skilled in the art, such as centrifugation, spinning, filtration, in such a manner as to obtain an extract free of solid particles. Advantageously, the liquid phase is recovered by centrifugation.

This solid-liquid separation step is followed by a step d) of purification by ultrafiltration, in order to eliminate the residual proteins and the denatured enzymes, using a membrane with a cutoff threshold between 10 and 15 kDa, preferably of 10 kDa, and recovery of the permeate. A diafiltration is advantageously carried out by diluting the retentate in order to improve the separation performances and thus recover a maximum of compounds of interest.

"Diafiltration" is understood to mean a rinsing of the retentate with a volume of water equal to the volume of this retentate, so as to facilitate passage and thus recover the maximum of molecules having a molecular weight below the threshold of filtration.

This step d) can also include a nanofiltration in order to optionally eliminate the free amino acids and the mineral salts. For example, the cutoff threshold will be between 100 Da (Daltons) and 300 Da, advantageously between 130 and 300 Da, and typically 200 Da.

In another embodiment, after the first step of ultrafiltration at 10 kDa, a second step of ultrafiltration through a 5 kDa membrane is carried out. This step makes it possible to recover the fraction of the retentate containing peptides and saccharides of which the molecular weight is between 5 kDa and 10 kDa.

Finally, the permeate of this ultrafiltration at 5 kDa is in turn purified by nanofiltration in order to eliminate free amino acids and minerals and obtain a hydrolysate including peptides and saccharides between 200 Da and 5 kDa.

The hydrolysate thus obtained can then moreover be diluted in water or in any mixture of solvents containing water. Thus, the cocoa hydrolysate according to the invention can advantageously be diluted in one or more physiologically acceptable solvents such as water, glycerol, ethanol, propanediol, butylene glycol, dipropylene glycol, ethoxylated or propoxylated diglycols, cyclic polyols or any mixture of these solvents.

A third subject matter according to the invention relates to a cosmetic composition, characterized in that it comprises, as active protective agent, an effective quantity of a hydrolysate of *Theobroma cacao* L. beans according to the invention, and a physiologically acceptable medium.

In a preferred embodiment according to the invention, the cocoa hydrolysate is present in the composition at a concentration from 0.001% to 20% with respect to the total weight of the composition, preferably from 0.1 to 10%, more preferably from 0.2 to 5%, even more preferably from 0.5 to 1.5%. For preparing the composition, the cocoa hydrolysate according to the invention can be in liquid or lyophilized form.

The compositions according to the invention are intended more particularly for administration by topical route. These compositions thus have to contain a cosmetically acceptable medium, that is to say a medium compatible with the skin and the keratinized skin appendages, and they cover all the cosmetic forms. These compositions can in particular be in the form of creams, oil-in-water emulsions, or water-in-oil or multiple emulsions, solutions, suspensions, gels, milks, lotions, sticks or also powders, and suitable for application to the skin, the lips and/or the keratinized skin appendages. These compositions include the excipients necessary for their formulation such as solvents, thickeners, diluents, surfactants, antioxidants, dyes, preservatives, perfumes. They can be used as skin care or skin makeup product.

The compositions according to the invention moreover comprise any additive commonly used in the application field in consideration as well as the adjuvants necessary for their formulation, such as solvents, thickeners, diluents, antioxidants, dyes, sunscreens, self-tanning agents, pigments, fillers, preservatives, perfumes, odor absorbers, cosmetic or pharmaceutical active ingredients, essential oils, vitamins, essential fatty acids, surfactants, film-producing polymers, etc.

The INCI Dictionary & Handbook ("International Nomenclature of Cosmetic Ingredients, 13th edition, 2010) published by "the Personal Care Products Council, Inc.," Washington, D.C.) describes a wide variety, without limitation, of cosmetic and pharmaceutical ingredients conventionally used in the skin care industry, which are suitable for use as additional ingredients in the compositions according to the present invention.

Non-limiting examples of these classes of additional ingredients include: the cicatrizing agents, the anti-aging agents, the anti-wrinkle agents, the anti-atrophy agents, the hydrating agents, the softening agents, the antibacterial agents, the antiparasitic agents, the antifungal agents, the fungicidal agents, the fungistatic agents, the bactericidal agents, the bacteriostatic agents, the antimicrobial agents, the anti-inflammatory agents, the antiprurigenous agents, the anesthetic agents, the antiviral agents, the keratolytic agents, the anti-free radical agents, the anti-seborrheic agents, the anti-dandruff agents, the agents modulating skin differentiation, proliferation or pigmentation, the penetration accelerating agents, the desquamation agents, the agents which stimulate or inhibit the synthesis of melanin, the bleaching agents, depigmentation agents or lightening agents, the pro-pigmentation agents, the self-tanning agents, the NO synthase inhibiting agents, the antioxidant agents, the free radical trapping and/or anti-atmospheric pollution agents, the anti-glycation agents, the firming agents, the agents stimulating the synthesis of dermal or epidermal macromolecules and/or the agents capable of preventing or inhibiting their degradation, the collagen synthesis stimulating agents, the elastin synthesis stimulating agents, the decorin synthesis stimulating agents, the laminin synthesis stimulating agents, the defensin synthesis stimulating agents, the chaperone synthesis stimulating agents, the aquaporin synthesis stimulating agents, the hyaluronic acid synthesis stimulating agents, the agents stimulating the synthesis of lipids and of components of the stratum corneum (ceramides, fatty acids, . . . ), the collagen degradation inhibiting agents, the elastin degradation inhibiting agents, the fibroblast proliferation stimulating agents, the keratinocyte proliferation stimulating agents, the adipocyte proliferation stimulating agents, the melanocyte proliferation stimulating agents, the keratinocyte differentiation stimulating agents, the adipocyte differentiation stimulating agents, the acetylcholinesterase inhibiting agents, the glycosaminoglycan synthesis stimulating agents, the DNA repair agents, the DNA protection agents, the anti-itch agents, the agents for the treatment and/or care of sensitive skin, the firming agents, the anti-stretch mark agents, the astringent agents, the sebum production regulating agents, the dermo-relaxant agents, the healing adjuvant agents, the re-epithelialization stimulating agents, the re-epithelialization adjuvant agents, the cytokine growth factors, the soothing agents, the anti-inflammatory agents, the agents acting on the capillary circulation and/or microcirculation, the angiogenesis stimulating agents, the vascular permeability inhibiting agents, the agents acting on cell metabolism, the agents intended for improving the dermo-epidermal junction, the agents inducing the growth of cranial hair and/or body hair, the agents inhibiting or slowing the growth of cranial hair and/or body hair, the myorelaxant agents, the anti-pollution and/or anti-radical agents, the lipolysis stimulating agents, the slimming agents, the anti-cellulite agents, the agents acting on the microcirculation, the agents acting on the cell metabolism, the cleaning agents, the hair styling agents, the hair growth stimulants, the sunscreens, the sunblocks, the makeup agents, the detergents, the pharmaceutical products, the emulsifying agents, the emollients, the organic solvents, the antiseptic agents, the deodorant active agents, the physiologically acceptable media, the surfactants, the abrasive agents, the absorbents, the aesthetic components such as perfumes, pigments, coloring agents, dyes and natural dyes, the essential oils, the texture agents, the cosmetic astringents, the anti-acne agents, the anti-coagulation agents, the anti-foaming agents, the antioxidants, the ligands, the biological additives, the enzymes, the enzymatic inhibitors, the enzymatic inducers, the coenzymes, the chelating agents, the plant extracts and plant derivatives, the essential oils, the marine extracts, the agents originating from a biofermentation and/or biotechnology process, the mineral salts, the cellular extracts, the sunscreens (the organic or mineral photoprotective agents which are active against ultraviolet A and/or B radiation), the ceramides, the peptides, the buffers, the volume agents, the chelating agents, the chemical additives, the dyes, the cosmetic biocides, the denaturing agents, the medicinal astringents, the external analgesics, the film-producing agents such as the polymers for enhancing the film-producing properties and the substantivity of the composition, the quaternary derivatives, the substantivity increasing agents, the opacifiers, the pH adjusting and regulating agents (example, triethanolamine), the propellants, the reducing agents, the sequestering agents, the skin bleaching and/or lightening agents, the skin conditioning agents (i.e., humectants, including miscellaneous and occlusive), the moisture retaining substances, the alpha hydroxyl acids, the beta hydroxyl acids, the hydrating agents, the epidermal hydrolytic agents, the soothing and/or cicatrizing agents, the skin treating agents, the anti-wrinkle agents, the agents capable of reducing or treating bags under the eyes, the exfoliation agents, the thickeners, the softeners, the gelling polymers, the vitamins and their derivatives, the wetting agents, the peeling agents, the soothing agents, the skin curing agents, the lignans, the preservatives (i.e., phenoxyethanol and parabens), the anti-UV agents, the cytotoxic, anti-neoplastic agents, the viscosity modifying agents, the nonvolatile solvents, the beading agents, the anti-perspiration agents, the depilatory agents, vaccines, perfumed water, skin restructuring agent, the excipients, the fillers, the minerals, the anti-mycobacterial agents, the anti-allergenic agents, the H1 or H2 antihistamines, the anti-irritation agents, the immune system stimulating agents, the immune system inhibiting agents, the insect repellent agents, the lubricants, the pigments or dyes, the hypopigmentation agents, the photostabilizing agents, and mixtures thereof, provided that they are physically and chemically compatible with the other ingredients of the composition and especially with the active substances of the present invention.

Moreover, the nature of these additional ingredients must not unacceptably alter the benefits of the active substances of the invention. These additional ingredients can be synthetic or natural such as, for example, plant extracts, or they can originate from a biofermentation process. Additional examples can be found in the INCI Dictionary & Handbook.

Such additional ingredients can be selected from the group including: the amino sugars, glucosamine, D-glucosamine, N-acetyl glucosamine, N-acetyl-D-glucosamine, mannosamine, N-acetyl mannosamine, galactosamine, N-acetyl galactosamine, vitamin B3 and derivatives thereof, niacinamide, sodium dehydroacetate, dehydroacetic acid and salts thereof, phytosterols, salicylic acid compounds, hexamidines, dihydroxyproline of dialkanoyl compounds, soybean extracts and derivatives, equol, isoflavones, flavonoids, phytantriol, farnesol, geraniol, bisabolol, peptides and derivatives thereof, di-, tri-, tetra-, penta- and hexapeptides and derivatives thereof, lys-thr-thr-lys-ser, palmitoyl-lys-thr-thr-lys-ser, carnosine, N-acyl amino acid compounds, retinoids, retinyl propionate, retinol, retinyl palmitate, retinyl acetate, retinal, retinoic acid, water-soluble vitamins, ascorbates, vitamin C, glucoside ascorbyl, palmitate ascorbyl, magnesium ascorbyl phosphate, sodium ascorbyl phosphate, vitamins and salts and derivatives thereof, provitamins and salts and derivatives thereof, ethyl panthenol, vitamin B and derivatives thereof, vitamin B 1, vitamin B2, vitamin B6, vitamin B12, vitamin K and derivatives thereof, pantothenic acid and derivatives thereof, pantothenyl ethyl ether, panthenol and derivatives thereof, ethyl panthenol, dexpanthenol, biotin, amino acids and salts and derivatives thereof, water-soluble amino acids, asparagine, alanine, indole, glutamic acid, water-insoluble vitamins, vitamin A, vitamin E, vitamin F, vitamin D and compounds thereof, mono-, di- and triterpenoids, beta-ionol, cedrol and derivatives thereof, water-insoluble amino acids, tyrosine, tryptamine, particulate materials, butylated hydroxytoluene, butylated hydroxyanisole, allantoin, tocopherol nicotinate, tocopherol, tocopherol esters, palmitoyl-gly-his-lys, phytosterol, hydroxyl acids, glycolic acid, lactic acid, lactobionic acid, ketoacids, pyruvic acid, phytic acid, lysophosphatidic acid, stilbenes, cinnamates, resveratrol, kinetin, zeatin, dimethylaminoethanol, natural peptides, the soybean peptides, salts of acid sugars, manganese gluconate, zinc gluconate, piroctone olamine, 3,4,4'-trichlorocarbanilide, triclocarban, zinc pyrithione, hydroquinone, kojic acid, ascorbic acid, magnesium ascorbyl phosphate, ascorbyl glucoside, pyridoxine, aloe vera, the alcohols of terpene, allantoin, bisabolol, dipotassium glycyrrhizinate, acid of glycerol, sorbitol, pentaerythritol, pyrrolidone and salts thereof, dihydroxyacetone, erythrulose, glyceraldehyde, tartaraldehyde, clove essence, menthol, camphor, eucalyptus essence, eugenol, menthyl lactate, hamamelis distillate, eicosene and vinyl pyrrolidone copolymer, iodopropyl butylcarbamate, a polysaccharide, an essential fatty acid, a salicylate, a glycyrrhetinic acid, carotenoids, ceramides and pseudo-ceramides, a complex lipid, oils of natural origin in general such as shea butter, apricot oil, onager oil, prune oil, palm oil, monoi oil, kahai oil, hydroquinone, HEPES, procysteine, O-octanoyl-6-D-maltose, disodium salt of methyl glycine diacetic acid, steroids such as diosgenin and the derivatives of DHEA, DHEA dehydroepiandrosterone and/or a chemical or biological precursor or derivative, N-ethylcarbonyl-4-para-aminophenol, blueberry extracts, phytohormones, *Saccharomyces cerevisiae* yeast extracts, extracts of algae, soybean, lupine, corn and/or pea, alverine and salts thereof, in particular alverine citrate, ruscus and horse chestnut extracts and combinations thereof, a metalloproteinase inhibitor, the *Schinus molle* extracts.

In all the cases, the person skilled in the art must ensure that these adjuvants as well as their proportions are chosen so as not to harm the desired advantageous properties of the composition according to the invention.

A fourth subject matter according to the invention relates to the cosmetic use of a composition according to the invention for protecting the skin from the harmful effects of blue light and for improving the barrier function of the skin, and for combating the appearance of the signs of aging and photoaging of the skin.

"Signs of aging of the skin" is understood to mean any modification of the external appearance of the skin due to chronological aging, such as wrinkles and small wrinkles, cracks, bags under the eyes, rings around the eyes, shriveling, loss of elasticity and/or tone of the skin, dulling or lack of shininess, pigmentary defects but also any internal modification of the skin which is not reflected systematically in a modified external appearance, such as, for example, thinning and loss of density of the dermis, thickening of the stratum corneum.

"Signs of photoaging of the skin" is understood to mean any degradation of the skin consecutive to exposure to UV radiation, such as the premature appearance of fine wrinkles around the eyes and the mouth and of expression wrinkles on the forehead; telangiectasia (small dilated blood vessels) on the nose, cheeks and neck, various pigmentary spots such as spots of redness and solar lentigo, irregularities in complexion, generalized loss of skin tone, increased tightness, loss of color or thinning of the skin of the lips, the skin can also thicken and become rough. Also covered is any internal modification of the skin which is not systematically reflected in a modified external appearance, such as, for example, thickening of the walls of the vessels, modification of the shape of the fibroblasts, slowing of collagen synthesis and disorganization of the collagen fibrils, accumulation of abnormal and amorphous material containing elastin (solar elastosis). For illustration, embodiments of the invention are described below.

EXAMPLE 1

Preparation of a Cocoa Hydrolysate from Cocoa Beans

The beans used include their shell and are of Peruvian origin, of the Criollo variety and more particularly of the Porcelana sub-variety.

The procedure is as follows:
a) Dissolution of cake of cocoa beans delipidated by pressing, at 10% dry matter (DM) in water;
b) Enzymatic hydrolysis of the carbohydrates by the action of a cocktail of cellulases (0.5%/DM) and pectinases (1.0%/DM), including a polygalacturonase, a pectin methyl esterase, a beta glucanase, a beta mannanase, a beta glucosidase, a cellulase, a hemicellulase, an arabanase and a xylanase, at a pH of 4.5 and a temperature of 55° C. for 2 hours;
c) Followed by enzymatic hydrolysis by an alkaline protease of the endopeptidase type (0.5% DM), at a pH of 9.0 and a temperature of 55° C. for 4 hours;
d) Thermal treatment at 85° C. for 45 minutes in order to denature the enzymes;
e) Centrifugation and recovery of the liquid phase;
f) Ultrafiltration and diafiltration of the liquid phase through a 10 kDa membrane and recovery of the permeate;
g) Nanofiltration of the permeate from ultrafiltration through a 200 Da membrane and recovery of the retentate.

The cocoa hydrolysate obtained in the retentate in step g) contains between 3.0 and 4.0% dry matter.

This dry matter comprises in particular 20 to 70% by weight of peptides and 5 to 40% of saccharides having a molecular weight between 200 Da and 10 kDa.

The hydrolysate can then be diluted in water in any water-containing mixture of solvents. Thus, the cocoa hydrolysate according to the invention can advantageously be diluted in one or more physiologically acceptable solvents such as water, glycerol, ethanol, propanediol, butylene glycol, dipropylene glycol, ethoxylated or propoxylated diglycols, cyclic polyols or any mixture of these solvents.

EXAMPLE 2

Preparation of a Cocoa Hydrolysate from Cocoa Beans

Steps a) to g) are identical to those carried out in Example 1. Then, the following procedure is carried out:
h) Lyophilization of the nanofiltration retentate with 50% by weight of maltodextrin (drying support) with respect to the dry extract of this retentate.

The cocoa peptide hydrolysate obtained in the retentate of step h) contains from 94.0 to 98.0% of dry matter.

This dry matter comprises in particular 50% maltodextrin, 10 to 35% by weight of peptides and 2 to 20% of saccharides having a molecular weight between 200 Da and 10 kDa.

EXAMPLE 3

Preparation of a Cocoa Hydrolysate from Cocoa Beans

Steps a) to g) are identical to those carried out in Example 2. Then, the following procedure is carried out:
h) Lyophilization of the nanofiltered retentate without drying support.

The cocoa peptide hydrolysate obtained in step h) contains between 94.0 and 98.0% dry matter.

This dry matter comprises in particular 20 to 70% by weight of peptides and 5 to 40% of saccharides having a molecular weight between 200 Da and 10 kDa.

EXAMPLE 4

Preparation of a Cocoa Hydrolysate from Cocoa Beans

Steps a) to f) are identical to those carried out in Example 1 for recovery of the ultrafiltrate 1. Then, the following procedure is carried out:

g) Ultrafiltration of the ultrafiltered permeate 1 through a 5 kDa membrane and recovery of the retentate.

h) Lyophilization of the ultrafiltered retentate 2 without drying support.

The peptide hydrolysate of cocoa obtained in step h) contains from 94.0 to 98.0% of dry matter having a molecular weight between 5 kDa and 10 kDa.

This dry matter comprises in particular 20 to 70% by weight of peptides and 5 to 40% of sugars.

EXAMPLE 5

Preparation of a Cocoa Hydrolysate from Cocoa Beans

Steps a) to f) are identical to those carried out in Example 1 for recovery of the permeate of the 10 kDa ultrafiltration (ultrafiltrate 1). The following procedure is then carried out:

g) Ultrafiltration 2 of ultrafiltrate 1 through a 5 kDa membrane and recovery of the permeate (ultrafiltrate 2);

h) Nanofiltration of the ultrafiltrate 2 through a 200 Da membrane and recovery of the retentate.

The peptide and saccharide hydrolysate of cocoa obtained in step h) contains from 3.0 to 4.0% of dry matter having a molecular weight between 200 Da and 5 kDa.

This dry matter comprises in particular 20 to 70% by weight of peptides and 5 to 40% of sugars.

EXAMPLE 6

Comparison of the Hydrolysate According to the Invention with the Extract Obtained According to FR2810242

The patent FR2810242, cited as prior art, proposes a cosmetic composition which contains a combination of 0.05 to 5% by weight of amino acids extracted from cocoa, 0.05 to 5% by weight of polyphenols extracted from cocoa, and 0.05 to 3% by weight of concentrate of unsaponifiables.

As comparison extract, a water-alcohol extract rich in polyphenols (referred to as polyphenol-rich extract in the following examples) according to the document FR2810242 was prepared as follows:

The polyphenols are extracted by maceration of the delipidated cake at 10% of dry extract in ethanol at 70% for 1 hour at 50° C., then the ethanol is evaporated under a vacuum.

The extract is then assayed by the Folin Ciocalteu method which makes it possible to assay all the polyphenols. The method uses gallic acid as standard, and the results are expressed in weight % of gallic acid equivalent.

The quantitative comparison of the two extracts is as follows.

The peptide and saccharide hydrolysate according to the invention is characterized:

by a content of polyphenols of 0.5% gallic acid equivalent. The composition which would contain 10% of the hydrolysate according to the invention would include a maximum of 0.05% of polyphenols. This corresponds to the minimum contents of FR2810242 between 0.5 and 5% to the nearest equivalencies (molecular weight of gallic acid compared to the molecular weight of the polyphenols present in the hydrolysate).

in that it contains: few or no free amino acids. They are in the form of peptides (partial hydrolysis of proteins).

in that it comprises no unsaponifiable compounds.

The qualitative comparison of the two extracts

It is important to note that the peptide and saccharide hydrolysate according to the invention contains few or no free amino acids. They are in the form of peptides (partial hydrolysis of proteins). Thus, in comparative terms, it is not justifiable to compare the amino acid content and the peptide content. However, it is interesting to compare the relative aminograms (relative profile of the amino acids represented in the two extracts).

The polyphenol profiles and the amino acid profiles of the hydrolysate according to the invention are given in FIG. 1A. This figure includes: the polyphenol profiles of the hydrolysate according to the invention and of the water-alcohol polyphenol-rich extract according to FR2810242. FIG. 1B includes the amino acid profiles of the completely hydrolyzed hydrolysate according to the invention and the aminogram results given in FR2810242.

The polyphenol-rich extract according to FR2810242 has a complex polyphenol profile with the potential presence of three families of molecules: flavonoids (for example, catechin and derivatives), phenyl propanoids (for example, ferulic acid and derivatives), and methyl xanthines (for example, caffeine and theobromine). By comparison, the polyphenol profile of the hydrolysate according to the invention no longer comprises flavonoids but still comprises the potential methyl xanthines and phenyl propanoids.

Conclusion:

The qualitative comparison of the hydrolysate according to the invention with a polyphenol-rich water-alcohol extract according to FR2810242 shows significant differences in terms of the polyphenol and amino acid (free or not) composition.

EXAMPLE 7

Evaluation of the Effects of a Peptide and Saccharide Hydrolysate of Cocoa According to Example 1 on the Level of Cellular Reactive Oxygenated Species Generated by Blue Light on Keratinocytes in Culture The purpose of this study is to evaluate the effect of a treatment by the cocoa hydrolysate according to example 1 on the level of oxidative stress generated by exposure to blue light in normal human keratinocytes in culture. In parallel, a treatment is carried out using a polyphenol-rich cocoa hydrolysate according to example 6.

A source of blue light consisting of LEDs is used to generate stress at 415 nm and 470 nm. The reactive oxygenated species (ROS) resulting from this exposure are determined at the cellular level by a fluorescent probe.

Protocol:

Normal human keratinocytes in culture are pre-treated by the hydrolysate according to example 1 diluted to 0.1% volume/volume (or to $1/1000^{th}$) in a specific culture medium, two times per day, while control cultures are maintained in an untreated condition. After 24 hours, a part of the control cultures and of the treated cultures is exposed to blue light (415 and 470 nm, at 3 mW/cm2 for 18 minutes), while the other part is maintained protected from light. After this exposure, the hydrolysate is applied again two times per day for 24 hours. Then, the exposure to blue light is repeated again, followed by the test of detection of the ROS.

For this purpose, the cells are put in the presence of a fluorescent probe (CellROX® Green Reagent, Lifetechnologies) for 30 minutes at 37° C. After fixation and rinsing, the cells are observed under an epi-fluorescence microscope (Zeiss Axiovert 200M microscope). A quantification of the intensity of the fluorescence, which is proportional to the quantity of ROS present, is carried out with the aid of the Volocity® image analysis software (PerkinElmer, Inc.) based on the photographs obtained.

Treatments in the presence of cocoa hydrolysates obtained according to examples 4 and 5 were also carried out. For this purpose, the hydrolysates were diluted beforehand in order to obtain a concentration comparable to the hydrolysate of example 1.

Results:

The treatment with the hydrolysate according to example 1 at 0.1% on keratinocytes makes it possible to significantly reduce the level of ROS generated by exposure to blue light (+90% of intensity in the cells exposed to blue light versus +34% in the treated and exposed cells, in comparison to the untreated control). In addition, the effect observed is greater than the effect obtained with the polyphenol-rich extract according to example 6 on these same cells.

A treatment by the hydrolysates obtained according to examples 4 and 5 also made it possible to observe a reduction of the level of ROS generated by exposure to blue light.

Conclusion:

The application of the hydrolysate of a cocoa hydrolysate obtained according to one of examples 1, 4 or 5 makes it possible to limit the oxidative stress generated by exposure to blue light, as indicated by the decrease in the level of intracellular ROS in the keratinocytes treated with the hydrolysate.

EXAMPLE 8

Evaluation of the Effects of a Cocoa Hydrolysate According to Example 1 on the Level of Mitochondrial Reactive Oxygenated Species Generated by Blue Light on Keratinocytes in Culture The purpose of this study is to evaluate the effect of a treatment by a cocoa hydrolysate according to example 1 on the level of oxidative stress generated by exposure to blue light, at the mitochondrial level, on normal human keratinocytes in culture. Indeed, the mitochondrion is a preferential target of the ROS, and damage to the mitochondrial DNA has been observed following exposure of epithelial cells of the retina to visible light[13]. In parallel, a treatment with a polyphenol-rich cocoa hydrolysate according to example 6 is carried out on these same cells.

Protocol:

The protocol of treatment of the cells and of exposure to blue light is identical to the one described in example 7. After these steps, the mitochondrial ROS are revealed by a fluorescent probe (MitoSOX™ Red Mitochondrial Superoxide Indicator, Invitrogen) put in contact with the cells for 15 minutes at 37° C. After rinsing and fixation, the cells are observed under the epi-fluorescence microscope (Zeiss Axiovert 200M microscope). A quantification of the intensity of the fluorescence, which is proportional to the quantity of ROS present, is carried out with the aid of the Volocity® image analysis software (PerkinElmer, Inc.) based on the photographs obtained.

Treatments in the presence of cocoa hydrolysates obtained according to examples 4 and 5 were also carried out. For this purpose, the hydrolysates were diluted beforehand to obtain a concentration comparable to the hydrolysate of example 1.

Results:

The exposure to blue light resulted in an increase of the mitochondrial ROS (+156% in comparison to the untreated control). In the presence of the cocoa hydrolysate according to example 1 at 0.1%, a strong decrease in the level of mitochondrial ROS is observed (+8% in comparison to the untreated control). The effect observed is greater than the effect obtained with the polyphenol-rich cocoa hydrolysate according to example 6 on these same cells.

A treatment with the hydrolysates obtained according to examples 4 and 5 also made it possible to observe a reduction of the level of ROS generated by exposure to blue light.

Conclusion:

In addition to the results reported in example 7, this test makes it possible to conclude that the application of the cocoa hydrolysate according to example 1, 4 or 5 makes it possible to limit the oxidative stress generated by exposure to blue light, as indicated by the decrease in the level of mitochondrial ROS.

EXAMPLE 9

Effect of the Cocoa Hydrolysate According to Example 1 on the Maintenance of the Level of Opsin-1, -2 and -3 After Exposure to Blue Light The purpose of this study is to observe the effect of exposure to blue light, as defined in examples 7 and 8, on the level of photoreceptors opsin-1, -2 and -3 in normal human keratinocytes treated by the cocoa hydrolysate according to example 1. These photoreceptors result from the expression of the OPN1-SW, OPN2 and OPN3 genes by the keratinocytes and are capable of inducing signaling pathways in the presence of the specific blue light wavelength of each opsin[12].

Protocol:

Normal human keratinocytes in culture are treated by the hydrolysate according to example 1 diluted to 0.1% volume/volume (or to $1/1000^{th}$), and are then exposed to blue light according to the protocol described in example 1. Three hours after the second exposure, a detection of opsin-1, opsin-2 and opsin-3 is carried out using an indirect immunofluorescence technique.

For this purpose, the cells are rinsed, fixed with paraformaldehyde at 3.7% and permeabilized with Triton at 0.1%, for 10 minutes. After saturation of the nonspecific sites with bovine serum albumin at 1% for 10 min, the cells are incubated with a solution of antibodies directed against opsin-1 (OPSN Short), opsin-2 (rhodopsin) or opsin-3 (pan-opsin) for one hour, then with a solution of secondary anti-rabbit antibody coupled to a fluorochrome (Alexa Fluor® 488, Invitrogen). The cells are then examined under the epi-fluorescence microscope (Zeiss Axiovert 200M microscope). A quantification of the fluorescence, with the aid of the Volocity® image analysis software (PerkinElmer, Inc.), is carried out based on the photographs obtained.

Treatments in the presence of cocoa hydrolysates obtained according to examples 4 and 5 were also carried out. For this purpose, the hydrolysates were diluted beforehand to obtain a concentration comparable to the hydrolysate of example 1.

Results:

In the presence of blue light under conditions determined to mimic over-exposure of the keratinocytes in culture, the labeling intensity of opsin-1 is significantly decreased with exposure at 415 nm, corresponding to the wavelength to which this opsin is sensitive (−33% compared to the control). Under the condition in which the cells had been treated with the cocoa hydrolysate according to example 1 at 0.1%, the labeling of opsin-1 is maintained (−10% in comparison to the control). Under the same conditions, the polyphenol-rich cocoa hydrolysate according to example 6 did not make it possible to observe a protective effect on the level of opsin-1(−33% in comparison to the untreated control).

Under identical treatment conditions, the intensity of the labeling of opsin-2 and of opsin-3 is decreased when the keratinocytes are exposed to blue light (470 nm) (−43% and −27%, respectively, in comparison to the untreated control). In the presence of the cocoa hydrolysate according to example 1 at 0.1%, the labeling of the opsins appears to be maintained (−28% and −10%, respectively, in comparison to the untreated control). Under the same conditions, the polyphenol-rich cocoa hydrolysate according to example 6 did not make it possible to observe a protective effect on the level of opsin-2 and opsin-3 (−42% and −30%, respectively, in comparison to the untreated control).

The results are presented in FIG. 2.

A treatment with the hydrolysates obtained according to examples 4 and 5 also made it possible to observe the maintenance of the levels of opsin-1, -2 and -3 after exposure to blue light.

Conclusion:

The cocoa hydrolysate obtained according to one of examples 1, 4 or 5 made it possible to maintain the levels of opsin-1, -2 and -3 in the presence of a stress mimicking over-exposure to blue light. These results demonstrate that the hydrolysate according to the invention has a protective effect with respect to blue light.

EXAMPLE 10

Effect of the Cocoa Hydrolysate According to Example 1 on the Level of Expression of the Circadian Proteins CRY-1 and PER-1 on Keratinocytes Exposed to Blue Light The present study consisted in evaluating the effect of the treatment by the cocoa hydrolysate according to example 1 on the maintenance of the level of the circadian proteins CRY-1 and PER-1 using keratinocytes subjected to exposure to blue light, under previously defined conditions for generating stress on these cells.

The modulation of the circadian genes is one of the consequences of the activation of the photoreceptors at the level of the cells of the retina. The expression of opsins in the retinal cells is itself dependent on the expression of the Clock gene, which is regulated by environmental factors such as exposure to light[13].

Protocol:

Normal human keratinocytes in culture are treated with the cocoa hydrolysate according to example 1 diluted to 0.1% volume/volume (or to 1/1000$^{th}$), and are then exposed to blue light according to the protocol described in example 7. Cultures treated under the same conditions are maintained in darkness. Six hours after the second exposure, the level of expression of the circadian proteins CRY-1 and PER-1 is revealed by the immunocytochemistry technique according to a standard protocol as described in example 9.

After rinsing, fixation and saturation of the nonspecific sites, the cells are incubated with primary antibodies directed against the proteins CRY-1 and PER-1, and then with secondary antibodies coupled to a fluorochrome (Alexa Fluor® 488, Invitrogen). The cells are then examined under the epi-fluorescence microscope (Zeiss Axiovert 200M microscope). A quantification of the fluorescence, with the aid of the Volocity® image analysis software (PerkinElmer, Inc.) is carried out based on the photographs obtained.

Treatments in the presence of cocoa hydrolysates obtained according to examples 4 and 5 were also carried out. For this purpose, the hydrolysates were diluted beforehand in order to obtain a concentration comparable to the hydrolysate of example 1.

Results:

Under the condition in which the cells are maintained in darkness, the cocoa hydrolysate according to example 1 at 0.1% made it possible to increase the level of expression of the proteins CRY-1 and PER-1 by +19% and +17%, respectively, in comparison to the untreated control. The exposure to blue light (415 nm) results in a significant decrease of CRY-1 (−25% in comparison to the unexposed cells) which is countered by the treatment with the cocoa hydrolysate according to example 1 (+20% in comparison to the unexposed and untreated control). Concerning the level of expression of PER-1, it is also decreased in the cells exposed to blue light (415 nm) (−11% in comparison to the unexposed cells) and appears to be maintained higher than the control under the condition with exposure and treatment with the hydrolysate (+27% in comparison to the unexposed and untreated control), under these same conditions.

A treatment with the hydrolysates obtained according to examples 4 and 5 also made it possible to observe the same results.

Conclusion:

The treatment with the cocoa hydrolysate obtained according to one of examples 1, 4 or 5 made it possible to maintain the level of the circadian proteins CRY-1 and PER-1 in the keratinocytes exposed to blue light. These results demonstrate that the hydrolysate according to the invention has a protective effect with respect to blue light.

EXAMPLE 11

Effect of the Cocoa Hydrolysate According to Example 1 on the Maintenance of the Fibrillin-1 Network in Ex Vivo Skin Biopsy Samples Exposed to UVB Stress or to Blue Light The purpose of this study is to evaluate a potential protective effect of the cocoa hydrolysate according to example 1 on the fibrillin-1 network in the presence of stress generated by UVB or by exposure to blue light.

The elastic fiber network appears to be a particular target of photoaging, in particular with regard to the changes in the structure of the microfibrils rich in fibrillin-1. This protein is a constituent of the oxytalan fibers present in the superficial dermis. With photoaging, the microfibrils of elastin lose their characteristic candelabra shape under the dermo-epidermal junction[14].

Protocol:

Human skin biopsy samples maintained in culture are treated 2 times per day for 24 hours with the cocoa hydrolysate according to example 1 diluted to 1% volume/volume (or to 1/100$^{th}$) in PBS, and are then irradiated with UVB (100 mJ/cm2) or exposed to blue light (470 nm, 3 mW/cm2 for 26 min). In parallel, biopsy samples are kept in darkness. The treatment is applied again 2 times per day for 24 hours, then the biopsy samples are subjected to a second exposure to UVB or to blue light. After another 24 hours of treatment, the biopsy samples are collected for fibrillin-1 detection by immunohistochemistry.

This technique is carried out using frozen sections incubated in the presence of the anti-fibrillin-1 antibody (murine monoclonal). After 1 hour of incubation followed by rinsings, the sections are incubated in the presence of the secondary anti-mouse antibody coupled to a fluorophore (Alexa Fluor® 488, Invitrogen). The sections are then examined under the epi-fluorescence microscope (Zeiss Axiovert 200M microscope). The network of elastin microfibrils present under the dermal-epidermal junction is then observed.

Treatments in the presence of cocoa hydrolysates obtained according to examples 4 and 5 were also carried out. For this purpose, the hydrolysates were diluted beforehand to obtain a concentration comparable to the hydrolysate of example 1.
Results:

For biopsy samples that remained in darkness, the microfibrils labeled with fibrillin-1 appear to be longer in the presence of the cocoa hydrolysate according to example 1 at 1%, compared to the untreated biopsy samples.

Under the condition in which the biopsy samples were exposed to UVB, the microfibril network appears clearly reduced and it is no longer possible to distinguish a perpendicular orientation of the fibers. Under the condition in which the biopsy samples were treated with the cocoa hydrolysate according to example 1 at 1% and exposed to UVB, longer fibers perpendicular to the dermo-epidermal junctions are observed, compared to the untreated exposed biopsy samples. These effects were also observed in the case of exposure to blue light.

A treatment with the hydrolysates obtained according to examples 4 and 5 also made it possible to observe the same results.
Conclusion:

These results indicate a protective effect of the cocoa hydrolysate obtained according to one of examples 1, 4 or 5, with regard to fibrillin-1, in the case of UVB stress and exposure to blue light, suggesting an advantage in the prevention of photoaging.

EXAMPLE 12

Effect of the Cocoa Hydrolysate According to Example 1 on the Level of Expression of Syndecan-4 in Ex Vivo Skin Biopsy Samples The purpose of the present study is to evaluate the potential effect of the cocoa hydrolysate according to example 1 on the level of syndecan-4 in human skin biopsy samples.

Syndecan-4 is a proteoglycan with heparane sulfate present on the cell surface where it plays the role of cell interaction mediator, regulating the mechanisms of cellular adhesion, migration, proliferation, endocytosis and mechanotransduction[15].
Protocol:

The human skin biopsy samples were treated with the cocoa hydrolysate according to example 1 diluted to 1% volume/volume (or to $1/100^{th}$) in PBS, 2 times per day, for a total of 72 hours.

The syndecan-4 was then revealed on sections of these biopsy samples by immunohistochemistry. For this purpose, the sections are put in contact with the primary antibody directed against syndecan-4 (rabbit polyclonal). After incubation and rinsings, a secondary anti-rabbit antibody coupled to a fluorophore (Alexa Fluor® 488, Invitrogen) is applied to the sections. The sections are then examined under the epi-fluorescence microscope (Zeiss Axiovert 200M microscope). A quantification of the fluorescence, with the aid of the Volocity® image analysis software (PerkinElmer, Inc.) is carried out based on the photographs obtained.
Results:

The cocoa hydrolysate according to example 1 made it possible to increase the level of syndecan-4 by +18% in comparison to the untreated control biopsy samples. This effect is observed to a lesser extent with the polyphenol-rich cocoa hydrolysate prepared according to example 6 (+12%).
Conclusion:

The cocoa hydrolysate according to example 1 has an activity on syndecan-4 in skin biopsy samples, suggesting a potential effect on the interactions between the keratinocytes and their extra-cellular environment.

EXAMPLE 13

In Vitro Tests Demonstrating the Anti-Aging and Rejuvenating Activity of the Cocoa Hydrolysate According to Example 2

The dermis provides a solid support for the epidermis in addition to being the element that feeds the epidermis. It consists mainly of fibroblasts and of an extracellular matrix consisting predominantly of collagens, of elastin and of a substance referred to as fundamental substance. These components are synthesized by the fibroblasts. The cohesion between the epidermis and the dermis is ensured by the dermo-epidermal junction.

Collagens are the predominant proteins of the extracellular matrixes of the skin. To date, 20 collagen types have been identified and labeled I to XX. The collagens present predominantly in the entire dermis are type I and III collagens which form the extracellular matrix of the entire dermis (these collagens make up 70-80% of the dry weight of the dermis). With aging, the dermis becomes thinner and wrinkles appear on the skin surface. Consequently, taking into account the important role of collagen in ensuring the integrity of the skin and its resistance to mechanical external aggression, the stimulation of the synthesis of these collagens and in particular of type I collagen appears to be an effective means for alleviating the signs of aging of the skin (review by Tzaphlidou M., *Micron* 35 (2004) 173-177).
1—Study of Young Cells Versus Aged Cells The following study made it possible to study the effect of the cocoa hydrolysate according to example 2 (referred to as hydrolysate in the figures) on the expression of collagen I, Elastin and Fibrillin 1, which are constituents of the extra-cellular matrix of the dermis, in order to evaluate its anti-aging and anti-photoaging activity and its rejuvenating activity. The latter activity was also evaluated by studying the effect of the cocoa hydrolysate according to example 2 on the methylation of DNA, epigenetic target.

In aging, the collagen fibers and the elastic fibers are altered due to reduced synthesis and increased degradation, resulting in reduced skin quality, with less tone and loss of elasticity.

To allow a claim of cellular Rejuvenation, we quantified the expression of the proteins involved in the structure of these fibers within cells aged intrinsically (replicative senescence) in the case of Collagen I and Elastin, or extrinsically by repeated UV irradiation (photo-aging) in the case of Fibrillin 1.

To understand the mechanism of the observed reactivation of the expression of the proteins, we conducted an analysis of DNA methylation on intrinsically aged cells. Indeed, one of the signatures of cellular senescence is the accumulation of methylated zones within the DNA, at the level of the Cytosines contained in the dinucleotides CpG. This results in the inactivation of promoters and in the decrease in the expression of certain genes.

Preliminary Evaluation of Cytotoxicity

The cytotoxicity of the molecules was evaluated on NHDF.

The cytotoxicity was evaluated at the maximum concentration tested which is soluble in an aqueous solution at 0.1% DMSO and at 7 dilutions from ½ log to ½ log.

The compound was put in contact with the cells for 24 hours. During the last 3 hours ready-to-use WST1 of the Roche® calorimetric test was introduced into the medium.

This reagent contains tetrazolium salts, a purple indicator. This reagent is cleaved to form formazan, a yellow indicator, by the metabolically active cells. The level of yellow coloration is thus proportional to the number of living cells. The absorbance measurement is performed at 450 nm.

The test considers a value of less than 90% of the control to indicate a possible cytotoxicity of the product (symbolized by a green line in the graphs). This can also indicate that the metabolic activity of the cells is decreased. A value of less than 75% indicates a significant cytotoxicity (symbolized by a red line in the graphs).

Moreover, the cells were observed under the microscope to observe and compare their physiognomy.

The cocoa hydrolysate according to example 2 exhibits a high cytotoxicity at 1000 ppm and a weaker but significant cytotoxicity between 200 and 20 ppm. The cocoa hydrolysate according to example 2 exhibits no significant cytotoxicity between 2 ppm and 20 ppm.

Concentrations Retained for Testing:

The cocoa hydrolysate according to example 2 is tested at the following concentrations 20-10-5 ppm.

Collagen I Targets

Collagen I is the predominant Collagen which gives its mechanical resistance to the skin.

This protein represents 90% of the collagen of a vertebrate. It constitutes the framework of the bone (comparable to the reinforcements of reinforced concrete) and more generally of the common connective tissues. It is found in the bones, the skin, the tendons, the cornea and the internal organs.

Method of Evaluation of the Effect of the Cocoa Hydrolysate According to Example 2 on the Expression of Collagen I Young NHDF (Normal Human Dermal Fibroblasts) or NHDF aged by replicative senescence were inoculated in 96-well plates and incubated for 24 h at 37° C., 5% CO2.

The cells were treated for 24 h in the presence of the test products.

The cells were then fixed with formalin, and the expression of the proteins was detected by immunofluorescence.

The fluorescent labels were imaged and quantified by automated microscopy (Arrayscan Cellomics™). The fluorescence was quantified by the bioapplication Compartimental Analysis.

Evaluation of the Effect of the Cocoa Hydrolysate According to Example 2 on the Expression of Collagen I The results are given in FIG. 3A.

The cocoa hydrolysate according to example 2 makes it possible to reactivate the expression of Collagen I in comparison to cells aged by replication. Indeed, the percentages of protein expression of the targeted protein obtained at the three tested concentrations of cocoa hydrolysate according to example 2 are higher than those obtained with the aged cell model.

Conclusion:

The cocoa hydrolysate according to example 2 is an ingredient which acts on collagen I, target of aging of the skin, by relaunching the protein expression in comparison to untreated aged cells and by partially reestablishing the protein expression in comparison to the young controls.

Elastin Target

Elastin is a structural glycoprotein (like laminin and fibronectin) entering in the composition of ECM. Elastin is a protein of the family of fibrous proteins of structural type. Secreted by the fibroblasts essentially during the growth period, it possesses elastic properties. Its synthesis decreases with age, and elastin is found to be replaced by inextensible collagen. Stretch marks are a visible example of this process which is associated with mechanical stresses. Aging of the skin is a second example of this.

In the extracellular matrix, elastin is synthesized and secreted in the extracellular space by the fibroblasts, first in the form of proelastin, and then in the form of tropoelastin. Elastin is the predominant component (up to 90%) of elastic fibers, in addition to fibrillin. Thus collagen associated with elastin and fibrillin which form the elastic fibers by transverse covalent bonds are the main constituents of the extracellular matrix. The total production of elastin stops around puberty. After this, the available quantity of elastin will decrease over time.

The degradation of elastin is connected with the action of elastase, an enzyme secreted by the fibroblasts. The enzymatic action of elastase is inhibited by $\alpha$1-antitrypsin. The inhibition of the degradation creates an equilibrium increasing the stability of elastin.

Distinctive features characterize elastin: elastin allows the cells to become connected and enables the formation of the biological tissues. Thus, the proper functioning of the skin, the lungs, the blood vessels, the connective tissues and of certain tendons and cartilages is closely connected with the features of elastin. As its name indicates, elastin is elastic. At equal diameter, it is 5 times more elastic than a rubber band. It can be stretched up to 150% of its length at rest before breaking. It thus allows the tissues to be stretched and to recover their initial state after stretching, which gives them flexibility.

Elastin is found in the dermis of the skin which acts as support. In aging, for example, the loss of elasticity and tone of the dermis, which can no longer oppose the effects of contraction of the underlying muscles, gives a rise to the appearance of wrinkles. In addition, exposure to ultraviolet radiation increases the degradation of elastin.

Method of Evaluation of the Effect of the Cocoa Hydrolysate According to Example 2 on the Expression of Elastin Young NHDF (Normal Human Dermal Fibroblasts) or NHDF aged by replicative senescence were inoculated in 96-well plates and incubated for 24 h at 37° C., 5% CO2.

The cells were treated for 24 h in the presence of the test products.

The cells were then fixed with formalin, and the expression of the proteins was detected by immunofluorescence.

The fluorescent labels were imaged and quantified by automated microscopy (Arrayscan Cellomics™). The fluorescence was quantified by the bioapplication Compartimental Analysis.

Evaluation of the Effect of the Cocoa Hydrolysate According to Example 2 on the Expression of Elastin The results are given in FIG. 3B.

The cocoa hydrolysate according to example 2 makes it possible to slightly reactivate the expression of Elastin in comparison to the aged cells.

Conclusion:

The cocoa hydrolysate according to example 2 is an ingredient which acts on Elastin, target of aging of the skin, by relaunching the protein expression slightly in comparison to untreated aged cells at the three concentrations tested and by partially reestablishing the protein expression in comparison to the young controls.

Fibrillin 1 Target

Fibrillin 1 is a protein which constitutes the microfibrils which are associated with the elastic fibers and participate in their assembly.

Method of Evaluation of the Effect of the Peptide Hydrolysate of Cocoa on the Expression of Fibrillin 1

Young NHDF (Normal Human Dermal Fibroblasts) or NHDF aged extrinsically by irradiation were inoculated in 96-well plates and incubated for 24 h at 37° C., 5% CO2.

The cells intended for extrinsic aging were irradiated 3 times with UVA with 24 h between each irradiation and 2 times with UVB with 48 h between each irradiation.

The cells were treated for 24 h in the presence of the test products.

The cells were then fixed with formalin, and the expression of the proteins was detected by immunofluorescence.

The fluorescent labels were imaged and quantified by automated microscopy (Arrayscan Cellomics™). The fluorescence was quantified by the bioapplication Compartimental Analysis.

Evaluation of the Effect of the Cocoa Hydrolysate According to Example 2 on the Expression of Fibrillin 1

The results are given in FIG. 3C.

The cocoa hydrolysate according to example 2 makes it possible to reactivate the expression of Fibrillin 1 in comparison to the aged cells.

Conclusion

The cocoa hydrolysate according to example 2 is an ingredient which acts on Fibrillin 1, target of aging of the skin, by relaunching its protein expression at the three concentrations tested in comparison to untreated aged cells and by reestablishing the protein expression almost completely in comparison to the young controls.

DNA Methylation Target

Methylation is a modification of the N-terminal ends of histones. It can take place either on lysines or on arginines and it can be materialized by the addition of one, two or three methyl groups. Depending on the methylated residues and the number of added groups, it is associated with activation or suppression of transcription. Histone methylation, which was considered to be static for a long time, turns out to be a reversible modification involved in a dynamic process, although it is more stable than acetylation and phosphorylation. An increasing number of histone demethylases have been identified. Generally, this type of modifications is antagonistic to acetylation, and the deacetylation of the lysines must precede their methylation. This antagonism results in the development of a certain dynamic equilibrium between the heterochromatin domains (which in general cannot be expressed and are methylated on certain key amino acids) and euchromatin domains (which in general can be expressed and are acetylated). For example, Lysine 9 of histone H3, when methylated, is known to be associated with a suppression of the surrounding chromatin. This methylation is recognized by a protein, HP1, which thus binds to methylated H3. HP1 in turn attracts the proteins Suv39, a histone methyltransferase, which will be able to methylate lysine 9 of histone H3 of the neighboring nucleosome, and so on. Thus, one can see how, step by step, the histones H3 will be methylated and the chromatin will be condensed. However, this heterochromatin invasion will be stopped if the encountered lysine 9 of H3 has already been acetylated. Thus, a competitive equilibrium develops between expressed and suppressed chromatin domains. The modifications of the histone tails play the role of epigenetic "marks" resulting in the recruitment of different classes of proteins, since the acetylated or methylated lysines are recognized by different protein domains. In addition, the recruitment of certain factors at the level of the chromatin requires the prior existence of modifications of histones and of proteins that are already bound. The code of the histones is thus interpreted in the context of other factors associated with the chromatin, and it is the combination of interaction between the modified histones and other factors that determines whether a protein is recruited for the chromatin. All the tissues of the organisms are affected by aging. This process is connected with the epigenetic modifications such as changes in methylation at the level of the specific cytosine residues of the DNA, as described in numerous publications. The role of epigenetic modifications on aging, the accumulation of cell divisions and of deteriorated macromolecules contribute to an aged phenotype. In addition, environmental and random events can modify this phenotype through the intermediary of epigenetic mechanisms such as DNA methylation and histone methylation and acetylation. The potential reversibility of the epigenetic modifications makes them attractive targets for the treatment of aging-associated pathologies.

Method of Evaluation of the Effect of the Cocoa Hydrolysate According to Example 2 on the Methylation of DNA Young NHDF (Normal Human Dermal Fibroblasts) or NHDF aged by replicative senescence were inoculated in 96-well plates and incubated for 24 h at 37° C., 5% CO2.

The cells were treated for 24 h in the presence of the test products.

The cells were then detached in the presence of trypsin and lysed. The genomic DNA was precipitated with Ethanol.

The level of methylation of DNA was assayed by ELISA using the Enzo kit: 5-Methylcytosine DNA ELISA kit. The values are represented starting from 50% on for better visibility of the results.

Evaluation of the Effect of the Cocoa Hydrolysate According to Example 2 on the Methylation of DNA The results are given in FIG. 3D.

The cocoa hydrolysate according to example 2 makes it possible to lower the methylation level in NHDF aged by replication to 10 and 5 ppm in order to come closer to the level observed in the young cells.

Conclusion

The cocoa hydrolysate according to example 2 is an ingredient which acts on the decrease of the methylation level of DNA which is a target of epigenetic aging, and thus it has a rejuvenation activity potential.

General Conclusion on the Anti-Aging and Rejuvenation Activity

In the course of aging, the collagen fibers and the elastic fibers are altered due to reduced synthesis and increased degradation. In order to demonstrate that the cocoa hydrolysate according to example 2 acts on cellular rejuvenation, a quantification was conducted of the expression of the proteins involved in the structure of these fibers within the cells aged intrinsically (replicative senescence), in the case of Collagen I and Elastin, or extrinsically by repeated UV irradiation (photo-aging) in the case of Fibrillin 1.

The cocoa hydrolysate according to example 2 makes it possible to relaunch the expression of the 3 markers.

In the context of the analysis of DNA methylation, the cocoa hydrolysate according to example 2 has homogeneous results in this experiment, it decreases methylation at 2 of 3 concentrations tested. This effect gives information on the mode of action of this product making it possible to reactivate the expression of proteins of the extracellular matrix, giving it its rejuvenation effect.

The hydrolysate of cocoa according to example 2 is consequently an active ingredient or substance which has an anti-aging and rejuvenating biological anti-age activity. It acts consistently on 3 targets of aging of the skin by relaunching the protein expression in comparison to the protein expression observed in the aged cells. It also has a novel activity on epigenetics, as demonstrated by its action on DNA methylation within mature cells. Finally, it demonstrates a deep anti-age action due to its efficacy on the synthesis of the proteins of the extracellular matrix.

EXAMPLE 14

Care Cream

| Ingredients or commercial name | INCI name | % w/w |
|---|---|---|
| Phase A | | |
| Purified water | Water/Aqua | Qs 100 |
| Na4 EDTA | Tetrasodium EDTA | 0.05 |
| Lubrasil** II MS free hydrogel | Water/aqua (and) Glycerin (and) Glyceryl Acrylate/Acrylic Acid Copolymer | 3.00 |
| LiquaPar/Rokonsal ™ MEP preservative | Phenoxyethanol (and) Methylparaben (and) Ethylparaben (and) Propylparaben | 1.00 |
| Phase B | | |
| UltraThix ™ P-100 polymer | Acrylic acid/VP Crosspolymer | 0.60 |
| Phase C | | |
| Sodium hydroxide | Sodium Hydroxide | 0.02 |
| Purified water | Water/Aqua | 0.50 |
| Phase D | | |
| Belsil ™ W3230* | Bis-Stearoxydimethylsilane (and) Stearyl Alcohol (and) Dimethicone | 2.00 |
| Simulsol ™ 165* | PEG-100 Stearate (and) Glyceryl Stearate | 2.00 |
| Refined shea butter | *Butyrospermum parkii* (Shea) Butter | 2.00 |
| Ceraphyl ™ 28 ester | Cetyl Lactate | 1.50 |
| Ceraphyl ™ 791 ester | Isocetyl Stearoyl Stearate | 2.00 |
| Ceraphyl ™ ODS ester | Octyldodecyl Stearate | 3.00 |
| Ceraphyl ™ 368 ester | Ethylhexyl Palmitate | 4.00 |
| Phase E | | |
| Sodium hydroxide | Sodium Hydroxide | 0.03 |
| Purified water | Water/Aqua | 0.50 |
| Phase F | | |
| Cocoa hydrolysate according to example 1 | | 1.00 |
| Total | | 100.00 |

Procedure

1. Pour phase A into the main container and start to homogenize. Heat to 70-75° C.

2. Drizzle into the UltraThix P-100 and thoroughly mix for approximately 30 min.

3. Add the ingredients of phase D to a second beaker and heat at 70-75° C.

4. Add the premixed phase C to phase A until the homogenization is complete.

5. At 70-75° C., add phase D to the main container and thoroughly mix. The emulsion must be perfectly homogeneous.

6. Start the cooling.

7. When the mixture reaches ~50° C., add premixed phase E and thoroughly mix.

8. At ambient temperature, add phase F and mix until a uniform mixture is obtained.

9. Stop at 25° C.

Properties:

Appearance: White cream pH: 5.2-5.6

Viscosity (D0) 25,000-50,000 (Brookfield RVT/Spindle B/5 RPM/1 minute/25° C.)

The preservation of this formula was validated by a double efficacy test over 28 days.

However, the preservatives were not optimized to their lowest level of effectiveness.

EXAMPLE 15

Protective Fluids for Outside Activities (In Vitro Sun Protection SPF 30)

| Ingredients or commercial name | INCI name | % w/w |
|---|---|---|
| Phase A | | |
| Purified water | Water/aqua | Qs 100 |
| EDTA, tetrasodium salt | Tetrasodium EDTA | 0.10 |
| Phase B | | |
| UltraThix ™ P-100 polymer | Acrylic acid/VP Crosspolymer | 0.50 |
| Phase C | | |
| Ceraphyl ™ 230 ester | Diisopropyl Adipate | 2.00 |
| Escalol ™ 517 UV filter | Butyl Methoxydibenzoylmethane (Avobenzone) | 3.00 |
| Escalol ™ 587 UV filter | Ethylhexyl Salicylate | 5.00 |
| Escalol ™ HMS UV filter | Homosalate | 10.00 |
| Escalol ™ 597 UV filter | Octocrylene | 7.00 |
| Escalol ™ S UV filter | Bis-Ethylhexyloxyphenol Methoxyphenyl Triazine | 4.00 |
| Phase D | | |
| DC FZ-3196* | Caprylyl Methicone | 6.00 |
| Eumulgin* VL 75 | Lauryl glucoside (and) Polyglyceryl-2 dipolyhydroxystearate (and) Glycerin | 4.00 |
| Natragem* E145 NP | Polyglyceryl-4 Laurate/Succinate (and) Aqua | 2.00 |

-continued

| Ingredients or commercial name | INCI name | % w/w |
|---|---|---|
| Phase E | | |
| Purified water | Water/aqua | 0.50 |
| Sodium Hydroxide | Sodium Hydroxide | 0.09 |
| Phase F | | |
| Methylparaben preservative | Methylparaben | 0.20 |
| Optiphen ™ ND preservative | Phenoxyethanol & Benzoic Acid & Dehydroacetic Acid | 1.00 |
| Phase G | | |
| Unicert* Yellow 08006-J (Sol. 1%) | Water/Aqua (and) CI 15985 (Yellow 6) | 0.80 |
| PF Sunny | Perfume/fragrance | 0.30 |
| Cocoa hydrolysate according to example 1 | Water/Aqua (and) Butylene Glycol (and) Theobroma cacao (cocoa) Seed Extract | 1.00 |
| Elixiance ™ biofunctional | Propanediol (and) Water/aqua (and) Schinus molle Extract | 1.00 |
| Gransil PSQ | Polymethylsilsesquioxane | 1.00 |
| Total | | 100.00 |

Procedure
1. Add water to the main container and add the ingredients of phase A at ambient temperature
2. Drizzle into phase A and mix to homogeneity
3. Add the ingredients of phase C to an adjacent container and heat to 65-70° C. by mixing, then cool to ambient temperature
4. At ambient temperature, homogenize phase C+ phase D
5. Add CD to the main container and thoroughly mix, until a homogeneous emulsion is obtained
6. Premix phase E and add to the main container while mixing
7. Premix phase F to 50° C., add to the main container while mixing
8. Add the ingredients of phase G one by one and thoroughly mix to homogeneity
9. Stop at 25° C.
Properties:
Appearance: Yellow fluid
pH: 5.5-6.0
Viscosity (D0) Brookfield RVT/Spindle 3/5 RPM/1 minute/25° C.: 5000-11,000 cps
The preservation of this formula was validated by a double efficacy test over 28 days.
However, the preservatives were not optimized to their lowest level of effectiveness.

BIBLIOGRAPHIC REFERENCES

1. Denda M, Fuziwara S. Visible radiation affects epidermal permeability barrier recovery: selective effects of red and blue light. J Invest Dermatol. 2008 May; 128(5):1335-6
2. Godley B F, Shamsi F A, Liang F Q, Jarrett S G, Davies S, Boulton M. Blue light induces mitochondrial DNA damage and free radical production in epithelial cells. J Biol Chem. 2005 June 3; 280(22):21061-6
3. Seko Y, Pang J, Tokoro T, Ichinose S, Mochizuki M. Blue light-induced apoptosis in cultured retinal pigment epithelium cells of the rat. Graefes Arch Clin Exp Ophthalmol. 2001 January; 239(1):47-52
4. Katz M L. Potential role of retinal pigment epithelial lipofuscin accumulation in age-related macular degeneration. Arch Gerontol Geriatr. 2002 May-June; 34(3):359-70
5. Kuse Y et al. Damage of photoreceptor-derived cells in culture induced by light emitting diode-derived blue light, Sci Rep. 2014 June 9; 4:5223
6. Kuse Y et al. Damage of photoreceptor-derived cells in culture induced by light emitting diode-derived blue light, Sci Rep. 2014 June 9; 4:5223
7. Kuse Y et al. Damage of photoreceptor-derived cells in culture induced by light emitting diode-derived blue light, Sci Rep. 2014 June 9; 4:5223
8. Fisher M R et al, Blue light irradiation suppresses dendritic cells activation in vitro. Exp Dermatol. 2013 August; 22(8):558-60
9. Gold, M H et al. Clinical Efficacy of Self-applied Blue Light Therapy for Mild-to-Moderate Facial Acne. J Clin Aesthet Dermatol. 2009 March; 2(3):44-50
10. Haltaufderhyde K et al. Opsin expression in human epidermal skin. Photochem Photobiol. 2015 January-February; 91(1):117-23
11. Poletini M O, Ramos B C, Moraes M N, Castrucci A M. Nonvisual Opsins and the Regulation of Peripheral Clocks by Light and Hormones. Photochem Photobiol. 2015 September-October; 91(5):1046-55
12. Haltaufderhyde K et al. Opsin expression in human epidermal skin. Photochem Photobiol. 2015 January-February; 91(1):117-23
13. Li P, Chaurasia S S, Gao Y, Carr A L, Iuvone P M, Li L. CLOCK is required for maintaining the circadian rhythms of Opsin mRNA expression in photoreceptor cells. J Biol Chem. 2008 Nov. 14; 283(46):31673-8
14. Langton A K, Sherratt M J, Griffiths C E, Watson R E. A new wrinkle on old skin: the role of elastic fibres in skin ageing. Int J Cosmet Sci. 2010 October; 32(5):330-9
15. Elfenbein A, Simons M. Syndecan-4 signaling at a glance. J Cell Sci. 2013 Sep. 1; 126(Pt 17):3799-804. Growth factors such as fibroblast growth factor (FGF), vascular endothelial growth factor (VEGF) and platelet-derived growth factor (PDGF) are mentioned in particular as ligand.

The invention claimed is:
1. A method for obtaining a peptide and saccharide hydrolysate of Theobroma cacao L. beans, characterized in that the peptides and saccharides have a molecular weight between 200 Da and 10 kDa, the method comprising:
   a) dispersing non-fermented, dried and crushed Theobroma cacao L. beans in an aqueous phase;
   b) enzymatically treating the aqueous dispersion obtained in step a) with a first treatment of at least one carbohydrase and then with a second treatment of at least one protease, wherein the carbohydrase is selected from the group consisting of a pectinase, a cellulase, an arabanase, a hemicellulase, a xylanase, a β-glucanase, and combinations thereof and the protease is of alkaline, neutral or acidic type;
   c) denaturing the enzymes by thermal treatment;
   d) recovering the enzymatic hydrolysate by solid/liquid separation;
   e) purifying the hydrolysate by ultrafiltration and nanofiltration.
2. The method of claim 1, wherein the beans of step a) are delipidated.
3. The method of claim 1, wherein the carbohydrase of step b) is a cocktail of carbohydrases including at least one polygalacturonase, a pectin methyl esterase, a beta glucanase, a beta mannanase, a beta glucosidase, a cellulase, a hemicellulase, an arabanase and a xylanase.

4. The method of claim 1, wherein the total enzyme concentration used in step b) of the method is between 0.1% and 3.0% by weight with respect to the weight of the beans to be treated.

5. The method of claim 4, wherein the carbohydrases of step b) include 0.5% by weight of the total dry matter weight of cellulases and 1% by weight of the total dry matter weight of pectinase.

6. The method of claim 1, wherein steps a) to d) of the method are carried out at a temperature between 20 and 90° C. and at a pH between 3.0 and 11.0.

7. The method of claim 1, wherein the solid/liquid separation of step d) is carried out by centrifuging, spinning, or filtering.

8. The method of claim 1, wherein in step e) the ultrafiltration is carried out with a cutoff threshold between 5 and 15 kDa, and the nanofiltration is carried out with a cutoff threshold between 100 Da and 300 Da.

9. The method of claim 1, wherein the protease is of the alkaline type with endopeptidase activity.

10. The method of claim 1, further comprising performing a lyophilization of the hydrolysate obtained in step e).

11. A peptide and saccharide hydrolysate of *Theobroma cacao* L. beans made by the method of claim 1.

12. A cosmetic composition comprising:
an effective quantity of a hydrolysate of *Theobroma cacao* L. beans made by the method of claim 1 as an active agent, and
a physiologically acceptable medium.

13. The cosmetic composition according to claim 12, wherein the hydrolysate of *Theobroma cacao* L. beans is present in the composition at a concentration from 0.001 to 20% with respect to the total weight of the composition.

14. The composition of claim 13, wherein the concentration of the hydrolysate of *Theobroma cacao* L. beans is from 0.1 to 10% with respect to the total weight of the composition.

15. The composition of claim 13, wherein the concentration of the hydrolysate of *Theobroma cacao* L. beans is from 0.2 to 5% with respect to the total weight of the composition.

16. The composition of claim 13, wherein the concentration of the hydrolysate of *Theobroma cacao* L. beans is from 0.5 to 1.5% with respect to the total weight of the composition.

17. The cosmetic composition according to claim 12, wherein the cosmetic composition is a topical composition for the skin.

18. The cosmetic composition according to claim 17, wherein topical application two times per day reduces cellular reactive oxygenated species generated by exposure to blue light.

* * * * *